United States Patent
Dado et al.

(10) Patent No.: US 7,256,306 B2
(45) Date of Patent: Aug. 14, 2007

(54) ARYLALKYLSULFONIC ACIDS AND METHODS FOR PRODUCING SAME

(75) Inventors: Gregory P. Dado, Chicago, IL (US); Randal H. Bernhardt, Antioch, IL (US)

(73) Assignee: Stepan Company, Northfield, IL (US)

( * ) Notice: Subject to any disclaimer, the term of this patent is extended or adjusted under 35 U.S.C. 154(b) by 443 days.

(21) Appl. No.: 10/484,757

(22) PCT Filed: Aug. 2, 2002

(86) PCT No.: PCT/US02/24562

§ 371 (c)(1),
(2), (4) Date: Jun. 17, 2004

(87) PCT Pub. No.: WO03/014070

PCT Pub. Date: Feb. 20, 2003

(65) Prior Publication Data

US 2004/0242920 A1    Dec. 2, 2004

(51) Int. Cl.
*C07C 309/00*    (2006.01)
(52) U.S. Cl. .......................................... 562/41; 562/30
(58) Field of Classification Search .................. 562/30, 562/41
See application file for complete search history.

(56) References Cited

U.S. PATENT DOCUMENTS

| | | | |
|---|---|---|---|
| 3,355,508 A | 11/1967 | Moulden | 585/311 |
| 3,502,716 A | 3/1970 | Kite | 562/117 |
| 3,585,253 A | 6/1971 | Huang et al. | 585/660 |
| 3,845,114 A | 10/1974 | Sweeney et al. | 562/108 |
| 3,951,823 A | 4/1976 | Straus et al. | 507/102 |
| 4,004,638 A | 1/1977 | Burdyn et al. | 166/270.1 |
| 4,220,204 A | 9/1980 | Hughes et al. | 166/270.1 |
| 4,415,504 A | 11/1983 | Chibata et al. | 562/41 |
| 4,536,301 A | 8/1985 | Malloy et al. | 507/259 |
| 5,049,311 A | 9/1991 | Rasheed et al. | 252/389.52 |
| 5,069,810 A | 12/1991 | Holmes et al. | 510/321 |
| 5,523,469 A | 6/1996 | Guyon | 562/41 |
| 6,043,391 A | 3/2000 | Berger et al. | |
| 2004/0011526 A1 | 1/2004 | Berger et al. | 166/275 |

FOREIGN PATENT DOCUMENTS

GB    568725 A    4/1945

OTHER PUBLICATIONS

Truce et al., Journal of Organic Chemistry (1962), 27, 3913-16.*
Archer S et al, "Condensation of Na 2-methyl-2-propenesulfonate with Aromatic Hydrocarbons", Journal of the American Chemical Society, vol. 67, pp. 43-45, coden: JACSAT, ISSN: 0002-7863, 1945, XP000984432.
International Search Report for PCT/US02/24562.
Vandoni et al., "Synthetic Detergents Behavior in the Agricultural Soil," Riv. Ital. Sostanze Grasse, 50(6) pp. 185-92 (1973).
C.W. Muth, "Synthesis of Polysulfonates for Enhancing Oil Recovery By Chemical Flooding," DOE/MC/11284-T4 (1980).
Ault, et al., JOACS, vol. 39, pp. 132-133 (1962).
P.D. Berger and C. H. Lee "New Surfactants for Improved Oil Recovery" in Progress in Mining and Oilfield Chemistry 2002, 4, 127-135.

* cited by examiner

*Primary Examiner*—Karl Puttlitz
(74) *Attorney, Agent, or Firm*—McAndrews, Held & Malloy Ltd.

(57) ABSTRACT

This invention relates new and improved processes for the preparation of arylalkylsulfonic acids derived from aromatic or substituted aromatic molecules and AOS acid (generally a mixture of alkenesulfonic acid and sultones, produced from the sulfonation of alpha olefins) and to cleaning compositions comprising said arylalkylsulfonic acids. The invention involves the use of a superacid catalyst to effectuate the conversion of AOS acid and aromatic reactants to arylalkylsulfonic acid under substantially anhydrous conditions, whereby a substantial improvement in the rate of conversion of the reactants to arylalkylsulfonic acid and/or improvement in mono-alkylation selectivity is realized, as compared to methods of preparation previously disclosed. Also useful as an alkylation promoter is the arylalkylsulfonic acid reaction product itself, produced in situ or from a previous reaction (i.e., a self-catalyst heel). The new processes generally afford arylalkylsulfonic acids with substantially improved conversion yields, highly desirable lighter color, and reduced odor, as compared to previously known methods. The acids produced by the inventive process may be neutralized to form arylalkylsulfonates (i.e., a neutralized form of the acid) which are useful in a variety of end use applications as surfactants and/or emulsifiers.

19 Claims, No Drawings

ARYLALKYLSULFONIC ACIDS AND METHODS FOR PRODUCING SAME

BACKGROUND OF THE INVENTION

1. Field of the Invention

This invention relates to arylalkylsulfonic acids and new and improved processes for the preparation of arylalkylsulfonic acids. These acids can be made from aromatic or substituted aromatic molecules and alpha olefin sulfonic acid ("AOS acid"; generally a mixture of alkenesulfonic acid and sultones, produced from the sulfonation of alpha olefins). More particularly, the invention relates to the use of a superacid catalyst (or an effective alkylation promoter) to effect the reaction of AOS acid and aromatic reactants to produce arylalkylsulfonic acids under substantially anhydrous conditions and to produce cleaning compositions derived therefrom.

2. Description of Related Art

Alkylbenzene sulfonic acids and the corresponding sulfonates (i.e., neutralized sulfonic acid) have found widespread use as surfactants in a variety of detergent, emulsion and industrial applications. These materials typically comprise a substituted aromatic ring, with an alkyl group at one position on the ring and a sulfonic acid moiety attached to another position on the ring; polyalkylates may also be present. Synthetic detergents based on the reaction of propylene tetramer and benzene using Lewis acid catalysts, such as $AlCl_3$ for example, were once widely used in laundry detergent formulations, but such use has diminished significantly due to environmental concerns. Also used in such formulations, although somewhat less popular, are alkylbenzene sulfonates based on branched alkyl groups. Linear alkylbenzenes starting materials which are based on the reaction of linear olefins (see, e.g., U.S. Pat. No. 3,585,253; to Huang, Jun. 15, 1971) or linear chloroparaffins (see, e.g., U.S. Pat. No. 3,355,508; to Moulden, Nov. 28, 1967) with benzene in the presence of a Lewis Acid catalyst are also well known in the surfactant art. These materials possess excellent detergency properties and are rapidly biodegradable. More recently, HF (or the Detal process variation) has become the alkylation catalyst of choice for the preparation of alkylated benzenes and other alkylated aromatic compounds, based upon environmental objections to the use of $AlCl_3$.

Detergent use is the predominant market for alkylbenzene sulfonates. However, these products are also employed in considerable quantities as additives in lubricants, coolants, industrial surfactant formulations, dispersants, emulsifiers, corrosion inhibitors and demulsifiers. Alkylbenzene sulfonates find widespread use in many industries among which are the petroleum recovery, refining, emulsion polymerization, textile dyeing, agriculture, institutional cleaning, drilling fluids, paper processing, coatings, and adhesives industries.

Present processes for producing alkylaromatics are designed to optimize the yields of detergent alkylate (predominantly monoalkylbenzene). The yields of heavy alkylate (predominantly dialkylbenzene) are therefore low. These heavy alkylates, however, find considerable demand as oil soluble surfactants and specialty chemicals. Dialkylbenzene sulfonates (see, e.g., U.S. Pat. Nos. 4,004,638; to Burdyn, et. al., Jan. 25,1977; 4,536,301; to Malloy, et. al., Aug. 20, 1985), alkyl xylene sulfonates (see, e.g., EP121964) and dialkyl phenol polyethoxy alkyl sulfonates (see, e.g., U.S. Pat. No. 4,220,204; to Hughes, et.al., Sep. 2, 1980) have all been used to increase the productivity of crude oil. Recently, U.S. Pat. No. 6,043,391; to Berger, et. al., Mar. 28, 2000, disclosed new sulfonic acid materials and processes for producing di- and tri-alkylbenzenes where both linear and branched alkyl groups are present on the same benzene ring.

Alkoxylated alkyl substituted phenol sulfonates have been produced and found to be useful as surfactants in numerous applications (see, e.g., U.S. Pat. No. 5,049,311; to Rasheed, et. al., Sep. 17, 1991, listing many uses for these compounds including use in enhanced oil recovery processes, as corrosion inhibitors, hydrotropes, foaming agents in concrete formation, surfactants for dye carriers, surfactants for fiber lubricants, surfactants for emulsion polymerization, as textile detergents, as foaming agents for drilling fluids, and as agricultural emulsifiers).

Alpha-olefin sulfonates (AOS) are widely used as surfactants in personal care, emulsion polymerization and firefighting foam applications, as well as a wide variety of other uses. These materials are typically produced on a commercial scale by sulfonating an alpha-olefin with $SO_3$, in a falling film sulfonator (see, e.g., Weil, Stirton and Smith; JOACS Vol 42, October 1965, pp 873-875, describing the reaction of hexadecene-1 and octadecene-1 with $SO_3$ followed by neutralization with NaOH to form the corresponding hexadecene sulfonates). The AOS precursor alpha-olefin sulfonic acid typically comprises alkene sulfonic acid and various sultones. As is well known to those of skill in the art, AOS correspondingly does not comprise a single component, but predominantly a mixture of two materials: an alkene sulfonate and a hydroxyalkane sulfonate. The hydroxyalkane sulfonate is present due to the formation of intermediate sultones when $SO_3$ reacts with the alpha olefin. Neutralization, with NaOH for example, not only neutralizes the alkene sulfonic acid formed during the sulfonation reaction, but also opens the sultone ring forming additional alkene sulfonate and hydroxyalkane sulfonate. Thus, neutralization results in a final product comprising approximately 60-70% alkene sulfonate, approximately 30% 3-, and 4-hydroxy sulfonate and approximately 0-10% disulfonate material; these percentages can vary greatly depending on the sulfonation and neutralization conditions which are utilized.

U.S. Pat. No. 3,845,114, to Sweeney, et. al., Oct. 29, 1974, teaches that the addition of limited amounts of water to alkene sulfonic acid with subsequent heating to 150° C. converts the sultone to alkene sulfonic acid and hydroxyalkane sulfonic acid. The presence of water during the ring-opening prevents dimerization of the alkene sulfonic acid. Removal of the water dehydrates the hydroxyalkane sulfonic acid back to sultone and alkene sulfonic acid, but leaves the already present alkene sulfonic acid intact. Repeating the process of adding limited amounts of water, heating to 150° C. and removing the water reduces the hydroxyalkane sulfonic acid content and increases the alkene sulfonic acid content. This "conversion" process is shown below in Scheme 1. Typically, for example, for a linear alkyl material, a may be an integer from 1 to 3 and b may be an integer from about 10 to 13, giving c+d=10-15. Very recently, U.S. Pat. No. 6,043,391 ("the '391 patent"); to Berger, et. al., Mar. 28, 2000, disclosed sulfonic acid materials and processes for producing such materials which required the use of this water/conversion process for the preparation of such materials. In the '391 patent, crude alkene sulfonic acid (containing significant amounts of sultone) produced from the reaction of an alpha-olefin and $SO_3$, is subjected to the aforementioned water addition and removal process for conversion of sultone to alkene sulfonic acid, which is then used to alkylate a variety of aryl compounds such as benzene, naphthalene, substituted benzene or substituted naphthalene.

Scheme 1: Conversion of Sultone to Alkene Sulfonic Acid

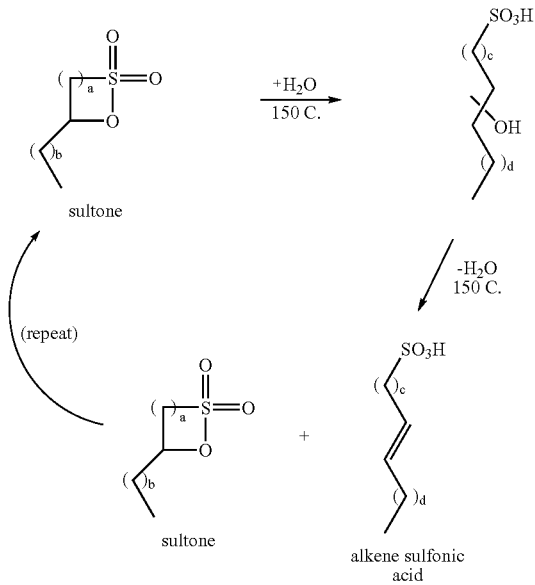

Ault, et. al., JOACS, Vol 39, February 1962, pp 132-133, describes the acid catalyzed addition of phenols and phenyl ethers to oleic acid. It was discovered that by using an acid catalyst, such as polyphosphoric acid or methane sulfonic acid, production of aryl substituted stearic acids was possible, as depicted in Scheme 2. Typically, for example, for a linear alkyl material, m+n may equal 14, thus o+p equal 15.

Scheme 2: Production of Aryl Substituted Stearic Acid

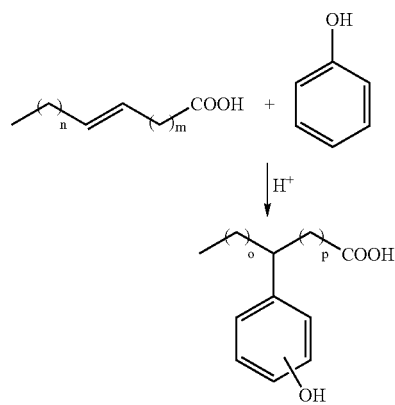

U.S. Pat. No. 3,502,716; to Kite, Mar. 24, 1970, discloses the use of alkali or alkaline earth metal carboxylates reacted at high temperature with hydroxy sulfonic acid anhydrides to produce the corresponding alkali or alkaline earth alkene sulfonate salts.

U.S. Pat. No. 3,951,823; to Straus, et. al., Apr. 20, 1976, teaches the reaction of AOS acid with itself and other sulfonated monomers to produce disulfonated dimers having good foaming properties for use in foam well cleanout applications. The '823 patent specifically requires that both monomers contain a sulfonate group and further teaches that suitable starting materials must contain at least about 5 nonaromatic carbon atoms per molecule, a sulfonate functional group, i.e., —$SO_3$—, and one of the following: (1) a carbon-carbon double bond, i.e., —CH=CH—; (2) an alkanol hydroxy group, or a sulfonate ester group of which the above sulfonate group is a component, i.e., a sultone, and the functional groups must be substituents attached to nonaromatic carbon atoms with the balance being carbon and/or hydrogen.

Also, as general alkene sulfonic acid and aromatic sulfonic acid background, see e.g., U.S. Pat. No. 2,336,113, Suter, C., Dec. 26, 1944, disclosing the condensation of olefin sulfonic acids with aromatic compounds; U.S. Pat. No. 3,845,114, Sweeney, et. al., Oct. 29, 1974 disclosing processes for conversion of sultones to alkene sulfonic acids; U.S. Pat. No. 3,721,707, Straus, et. al., Mar. 20, 1973, describing organic sulfonic acid oligomers and processes for producing same; U.S. Pat. No. 3,873,590, Straus, et. al., Mar. 25, 1972, describing methyl esters of sulfonic acid oligomers; U.S. Pat. No. 3,875,102, Straus, et. al., Apr. 1, 1975, describing use of methyl esters of sulfonic acid oligomers plasticized with polyvinyl chloride; U.S. Pat. No. 3,953,338, Straus, et. al., describing the use of oligomeric sulfonic acids for foam well cleanout; and U.S. Pat. No. 5,034,161, Alink, B. A., Jul. 23, 1991, describing the synthesis of aryl-substituted aliphatic acids.

The forgoing references teach several ways in which alkene sulfonic acid materials can be reacted with aromatic materials to produce derivative sulfonic acid materials. However, to date, prior processes have required the conversion of crude acid from the reaction of an alpha-olefin and $SO_3$, via the repeated hydrolysis and dehydration with water, resulting in the formation of alkene sulfonic acid as taught by U.S. Pat. No. 3,845,114. Such conversion is time consuming, inconvenient, and on a commercial scale, can be quite costly. Additionally, prior alkene sulfonic acid alkylation processes have failed to produce alkylated products with high reaction throughput rates (i.e. yields) and/or high levels of selectivity toward the desired mono-alkylate products, versus undesirable dialkylate and/or AOS acid dimmer/oligomer materials. Typically, prior art processes which attempted to increase selectivity toward mono-alkylate production via the use of excess aromatic compound were not successful and lower rates were typically obtained.

In view of the limitations associated with previously known alkene sulfonic acid processing technologies, a need exists for a superior alkylation process whereby a substantial improvement is realized in terms of the reaction rate and reaction product selectivity. Additionally, there is a need for an alkene sulfonic acid alkylation process which does not require tedious conversion of crude alkene sulfonic acid (i.e., conversion whereby water is added and removed in a cyclic manner (and heating is applied) to and from the crude AOS acid to convert the sultone to alkene sulfonic acid) prior to alkylation. Further, there is a need for an alkene sulfonic acid alkylation process which does not require digestion of the crude alkene sulfonic acid prior to its use in the alkylation process.

SUMMARY OF THE INVENTION

This invention provides arylalkylsulfonic acids and new and improved processes for the preparation of arylalkylsulfonic acids derived from aromatic (or substituted aromatic) molecules and AOS acid. It has been surprisingly discovered that crude AOS acid, which contains an appreciable amount of sultone material, can be directly employed in the production of arylalkylsulfonic acids without the use of water addition/removal conversion cycles.

In accordance with this discovery, the invention provides the use of a superacid catalyst (or an alkylation promoter) to effectuate the conversion of AOS acid and aromatic reactants to arylalkylsulfonic acid under substantially anhydrous conditions, whereby a substantial improvement in the rate (and monoalkylation selectivity) of conversion of the reactants to arylalkylsulfonic acid is realized, as compared to methods of preparation previously known. The processes of the invention generally do not require an AOS acid conversion step (i.e., conversion, whereby water is added and removed in a repeated cyclic fashion, along with heating, to and from the crude AOS acid to convert the sultone to alkene sulfonic acid) prior to alkylation. Additionally, the processes of the invention do not require that the AOS acid be digested (defined hereinafter) prior to use in the alkylation reaction.

Accordingly, the invention provides methods for preparing an arylalkylsulfonic acid comprising alkylating an aromatic compound with an AOS acid in the presence of a superacid catalyst at a temperature sufficient to produce an arylalkylsulfonic acid, wherein the alkylation is conducted under substantially anhydrous conditions.

The invention further comprises the use of arylalkylsulfonic acid (AASA) compositions in formulations intended for laundry, cleaning, and personal care applications. More particularly, this invention relates to the use of AASA compositions as a component in formulations for fabric cleaning and care, hard surface cleaning and care, and personal care, including, but not limited to: solvent-free-all-purpose cleaners, solvent-containing-all-purpose cleaners, pine oil cleaner concentrates, "economy", "ultra", and "premium ultra" light-duty liquid dish detergents, "premium" and "economy" heavy-duty laundry powder detergents, unbuilt and built "economy" heavy-duty laundry liquid detergents, "premium" heavy-duty laundry liquid detergents, shampoo, hand soap, and body wash.

Generally, the aromatic compound is selected from the group consisting of benzene, a mono-substituted aromatic compound, a poly-substituted aromatic compound, alkylbenzene, alkoxylated benzene, a polycyclic aromatic compound, a mono-substituted polycyclic aromatic compound, a poly-substituted polycyclic aromatic compound, naphthalene and alkylnaphthalene, or a mixture thereof.

The AOS acid typically comprises an alkene sulfonic acid, a sultone or a mixture thereof. The AOS acid may also be predominantly sultone material. The superacid catalyst is generally selected from the group consisting of a solid super-acid, a perfluorosulfonic acid resin (e.g., Nafion® NR50, a registered trademark of E.I. duPont de Nemours Co.), a supported perfluorosulfonic acid resin, a metal sulfate, zirconium sulfate, zirconium tungstate, a superacid zeolite, a sulfated metal oxyhydroxyide, a sulfated metal oxysilicate, a superacid metal oxide, $CF_3SO_3H$ or a mixture thereof.

As previously stated, it has been surprisingly discovered that the processes of the invention generally do not require an AOS acid conversion step. Although less preferred and also not required, the method can optionally further comprise digesting (distinct from conversion and defined hereinafter) the AOS acid, optionally in the presence of water, and optionally in the presence of the aromatic compound, and if present, removing said water prior to alkylation, such that the alkylation is conducted under substantially anhydrous conditions.

It is a further object of the invention to provide a method for preparing an arylalkylsulfonic acid, comprising:
a) sulfonating an alpha olefin to form an AOS acid;
b) alkylating an aromatic compound with the AOS acid in the presence of a superacid catalyst, wherein the alkylation is conducted under substantially anhydrous conditions and at a temperature sufficient to produce an arylalkylsulfonic acid.

The processes of the invention may also comprise alkylating the aromatic compound with an AOS acid in the presence of an alkylation promoter comprising the arylalkylsulfonic acid itself, i.e., a reaction heel, either from a previous preparation or prepared concurrently in the process being practiced. These embodiments may also include the use of a superacid catalyst in combination with the alkylation promoter.

It is further an object of the invention to provide arylalkylsulfonic acids produced by the processes disclosed herein. Another object of the invention is to provide arylalkylsulfonates produced by neutralization of the arylalkylsulfonic acids from the processes disclosed herein. A further object of the invention is a detergent or emulsion composition comprising such sulfonates.

The reaction of AOS acid with an aromatic compound, in the presence of the superacid catalyst (or arylalkylsulfonic acid alkylation promoter heel), may be carried out in batch mode, semi-continuous or in a continuous flow process such as provided by, for example, a continuous stirred tank reactor. In addition to improved rates of conversion, the new processes generally afford arylalkylsulfonic acids with substantially higher conversion yields, highly desirable lighter color and reduced odor, as compared to previously known methods for preparing such acids.

Further, the invention allows for achievement of higher selectivity (i.e., monoalkylation) via use of excess aromatic, while at the same time achieving excellent reaction rates. This discovery is especially surprising, as in previously known methods, the use of excess aromatic dramatically slows reaction rates such that the reaction is not commercially practical or such that very high reaction temperatures are needed, resulting in very poor product color and odor.

These and other objects and advantages are achieved by the invention description below.

DETAILED DESCRIPTION OF THE INVENTION

The invention provides a method for preparing an arylalkylsulfonic acid comprising alkylating an aromatic compound with an AOS acid in the presence of a superacid catalyst and at a temperature sufficient to produce an arylalkylsulfonic acid, wherein the alkylation is conducted under substantially anhydrous conditions. Typically, the molar ratio of aromatic compound to AOS acid is from about 0.5:1 to about 30:1. Ideally, the molar ratio of aromatic compound to AOS acid is from about 2:1 to about 10:1.

The aromatic compound is generally an aromatic hydrocarbon, selected from the group consisting of benzene, a mono-substituted aromatic compound, a poly-substituted aromatic compound, alkylbenzene, alkoxylated benzene, a polycyclic aromatic compound, a mono-substituted polycyclic aromatic compound, a poly-substituted polycyclic aromatic compound, naphthalene and alkylnaphthalene, or a mixture thereof. More specifically, the aromatic compound is selected form the group consisting of benzene, toluene, xylene, cumene, ethyl benzene, propylbenzene and naphthalene, or a mixture thereof. Still more preferably, the aromatic compound is benzene, toluene, or xylene. The aromatic compound may also be selected from the group consisting of phenol, alkylphenol alkylated on one or more carbons, and alkoxylated phenol.

An alkoxylated phenol is a polyoxyalkylenephenol ether derived from the reaction of the phenolic OH group with ethylene oxide, propylene oxide, butylene oxide and mixtures thereof.

The AOS acid generally comprises an alkene sulfonic acid, a sultone or a mixture thereof. The sultone is generally of the formula:

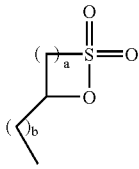

and the alkene sulfonic acid is generally of the formula:

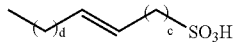

wherein a is 1, 2 or 3 and b is an integer 1 to 31; wherein c and d are independently integers 0 to 33, provided that c+d=1 to 33. Typically, although not necessarily critical, the molar ratio of alkene sulfonic acid to sultone is from about 1:1 to about 1:4.

When a is 1, a β-sultone is formed.
When a is 2, a γ-sultone is formed.
When a is 3, a δ-sultone is formed.

The superacid catalyst is selected from the group consisting of a solid superacid, a perfluorosulfonic acid (e.g., Nafion® NR50) or a resin thereof, a superacid zeolite, a supported perfluorosulfonic acid resin, a metal sulfate, zirconium sulfate, zirconium tungstate, a sulfated metal oxyhydroxyide, a sulfated metal oxysilicate, a superacid metal oxide, $CF_3SO_3H$, or a mixture thereof. Generally, the perfluorosulfonic acid resin is a copolymer of sulfonyl fluorovinyl ether and a fluorocarbon.

The arylalkylsulfonic acid comprises a compound of the formula:

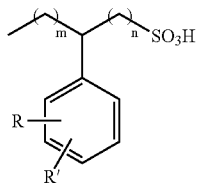

wherein m and n are independently integers 0 to 34, provided that m+n is at least 2 and wherein m+n is equal to or less than 34; wherein R and R' are independently selected from H, alkoxy, OH, $C_1$-$C_{36}$ alkyl, substituted $C_1$-$C_{36}$ alkyl and polyoxyalkylene ether.

Polyoxyalkylene ethers are derived from the reaction of an OH group with ethylene oxide, propylene oxide, butylene oxide and mixtures thereof. The polyoxyalkylene ether may contain an either an OH group or a $C_1$-$C_4$ alkoxy group. Examples of polyoxyalkylene ethers include —O—$(CH_2CH_2O)_n$—$(CH_2CH(CH_3)O)_p$—H, —O—$(CH_2CH_2O)_n$—$(CH_2CH(CH_3)O)_p$—O—$(CH_2CH_2O)_n$—H, —O—$(CH_2CH(CH_2CH_3)O)_q$—$(CH_2CH(CH_3)O)_p$—H, —O—$(CH_2CH_2O)_n$—H, —O—$(CH_2CH_2O)_n$—$(CH_2CH(CH_3)O)_p$—$(CH_2CH(CH_2CH_3)O)_q$—H, and —O—$(CH_2CH_2O)_n$—$C_1$-$C_4$ alkyl wherein n, p, and q at each occurrence are independently 0 or an integer from 1 to about 30. One of skill in the art will appreciate that polyoxyalkylene ethers other than those exemplified above are readily prepared and are contemplated by the instant application. For example, one of skill in the art would recognize that the order of the groups can be altered.

The substituted alkyl must be substituted with at least one and no more 7 groups independently selected from $CO_2H$ and salts thereof, $C_3$-$C_6$ alkoxy, $CONH_2$, $CONH(C_1$-$C_6$ alkyl), $CON(C_3$-$C_6$ alkyl)($C_1$-$C_6$ alkyl), CN, halide, OH, $C_1$-$C_6$ alkoxycarbonyl, oxo, $SO_3H$, SH, —S-alkyl, —SO-alkyl, polyoxyalkylene ether, and —$SO_2$-alkyl. Preferably, the substituted alkyl is substituted with 1-5 groups independently selected from $CO_2H$, $C_1$-$C_6$ alkoxycarbonyl, OH, polyoxyalkylene ether, and $SO_3H$. Even more preferably, the substituted alkyl group is substituted with 1-3 groups independently selected from $CO_2H$, $C_1$-$C_6$ alkoxycarbonyl, OH, polyoxyalkylene ether, and $SO_3H$. Still more preferably, the substituted alkyl group is substituted with 1 or 2 groups independently selected from $CO_2H$, $C_1$-$C_6$ alkoxycarbonyl, OH, polyoxyalkylene ether, and $SO_3H$. Still more preferably, the substituted alkyl group is substituted with $CO_2H$ or $SO_3H$.

Typically, processes of the invention provide this material as the primary component in excess of 30% by weight, and ideally in excess of 50% by weight, based on the total weight of the arylalkylsulfonic acid.

The arylalkylsulfonic acid may further comprise a compound of the formula:

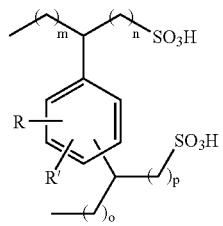

wherein m and n are independently 0-34, provided that m+n is at least 2 and wherein m+n is equal to or less than 34; wherein o and p are independently 0-34, provided that o+p is at least 2 and wherein o+p is equal to or less than 34; wherein R and R' are independently selected from H, $C_1$-$C_6$ alkoxy, OH, $C_1$-$C_{36}$ alkyl, substituted $C_1$-$C_{36}$ alkyl and polyoxyalkylene ether. Ideally, processes of the invention provide this material as a minor component relative to the monoalkylate material.

The arylalkylsulfonic acid may further comprise an AOS acid dimer compound of the formula:

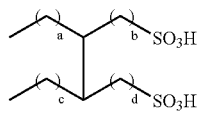

wherein a and b are independently 0-34, provided that a+b is at least 2 and wherein a+b is equal to or less than 34; wherein c and d are independently 0-34, provided that c+d is at least 2 and wherein c+d is equal to or less than 34. Although the above structure indicates a dimer acid connected by one carbon-carbon bond, two acid molecules may be connected together by two carbon-carbon bonds, thereby producing a cyclic type dimer acid (oligomeric acids are also contemplated). Again ideally, processes of the invention provide this material as a minor component relative to the monoalkalkylate material.

Typically, the alkylation processes detailed herein are conducted at a temperature from about 80° C. to about 200° C.; the alkylation is always conducted at a temperature below the decomposition temperature of the reactants or products. Ideally, the alkylation is conducted at a temperature from about 100° C. to about 150° C.

In another embodiment, the invention further provides a method for preparing an arylalkylsulfonic acid, comprising:
a) sulfonating an alpha olefin to form an AOS acid;
b) alkylating an aromatic compound with the AOS acid in the presence of a superacid catalyst, wherein the alkylation is conducted under substantially anhydrous conditions and at a temperature sufficient to produce an arylalkylsulfonic acid. In accordance with this embodiment, the aromatic compound is selected from the group of materials previously defined above, with the AOS to aromatic ratio as previously defined. Further, the AOS acid comprises an alkene sulfonic acid, a sultone or a mixture thereof, as previously discussed; the sultones and alkene sulfonic acids are of the formulas and present in the ratios as detailed above. The superacid catalysts useful in accordance with this embodiment are the same as those previously described; the temperature at which the alkylation is conducted is as previously detailed. Additionally, the arylalkylsulfonic acid comprises compounds similar to those described above. The alpha olefins useful in this embodiment are of the formula

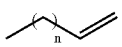

wherein n=1-33. Additionally, branched olefins may be used, as well as internal olefins which are either linear or branched; vinylidines may also be used.

In yet another embodiment, the invention provides a method for preparing an arylalkylsulfonic acid comprising alkylating an aromatic compound with an AOS acid in the presence of an alkylation promoter comprising a compound of the formula:

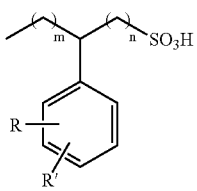

wherein m and n are independently integers 0 to 34, provided that m+n is at least 2 and wherein m+n is equal to or less than 34; wherein R and R' are independently selected from H, $C_1$-$C_6$ alkoxy, OH, $C_1$-$C_{36}$ alkyl, substituted $C_1$-$C_{36}$ alkyl and polyoxyalkylene ether, wherein the alkylation is conducted at a temperature sufficient to produce an arylalkylsulfonic acid; and wherein the alkylation is conducted under substantially anhydrous conditions; and wherein the alkylation promoter is initially present in at least about 25% by weight, based on the weight of the AOS acid present.

By initially present is meant that the AOS acid and the aromatic compound are added to a reaction vessel that already contains the alkylation promoter or the alkylation promoter is added to a reaction vessel that contains the AOS acid and/or the aromatic compound prior to the commencement of the reaction between the AOS acid and the aromatic compound. Preferably, the alkylation promoter is present in the reaction vessel when the OAS acid and the aromatic compound are combined.

Ideally, the alkylation promoter is initially present in at least a 1:1 ratio with the AOS acid. Most ideally, the alkylation promoter is initially present in at least a 2:1 ratio with the AOS acid present. The alkylation promoter may be prepared in situ during an alkylation reaction or may originate from a previous arylalkylsulfonic acid formation reaction.

The term "alkylation promoter" as used herein means the materials described above and below, wherein such materials are anhydrous or substantially anhydrous acid materials which are capable of effectuating the alkylation reaction to produce an arylalkylsulfonic acid with the requisite properties, i.e., selectivity, yield, color, etc.

In accordance with this embodiment, the alkylation promoter may further comprise a compound of the formula:

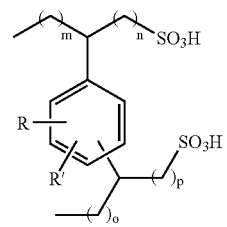

wherein m and n are independently 0-34, provided that m+n is at least 2 and wherein m+n is equal to or less than 34; wherein o and p are independently 0-34, provided that o+p is at least 2 and wherein o+p is equal to or less than 34; wherein R and R' are independently selected from H, $C_1$-$C_6$ alkoxy, OH, $C_1$-$C_{36}$ alkyl, substituted $C_1$-$C_{36}$ alkyl and polyoxyalkylene ether.

Further, the alkylation promoter may comprise a compound of the formula:

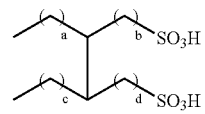

wherein a and b are independently 0-34, provided that a+b is at least 2 and wherein a+b is equal to or less than 34; wherein c and d are independently 0-34, provided that c+d is at least 2 and wherein c+d is equal to or less than 34. Again, this dimer acid material may contain a cyclic type structure as previously discussed above, and/or may be oligomeric in nature.

Further in accordance with this embodiment, the AOS acid comprises an alkene sulfonic acid, a sultone, with the structures/formulas for such materials being as previously defined, or a mixture thereof. The alkylation promotion agent may further comprise a superacid catalyst, such as those previously described.

In another embodiment, the invention provides a method for preparing an arylalkylsulfonic acid comprising a) sulfonating an alpha olefin to form an AOS acid which comprises an alkene sulfonic acid and a sultone;

b) alkylating an aromatic compound with the AOS acid in the presence of an alkylation promoter, wherein the alkylation is conducted at a temperature sufficient to produce an arylalkylsulfonic acid, and wherein the alkylation is conducted under substantially anhydrous conditions. The alpha olefin, alkene sulfonic acid, sultone, the alkylation promoter and arylalkylsulfonic acid are as previously defined. This embodiment may further comprise the use of a previously identified superacid catalyst in combination with the alkylation promoter.

The invention provides arylalkylsulfonic acids produced by the processes identified herein.

Aromatic Compounds

The aromatic compound may generally be any compound which is capable of being alkylated with an alkene sulfonic acid (which comprises alkene sulfonic acid molecules and sultones, or alternatively a material which predominantly comprises sultones). Generally, and in addition to any of the compounds previously identified, the aromatic compound can be any one of those identified and produced in U.S. Pat. No. 5,146,026; Berna Tejero, et. al., Sep. 8, 1992; U.S. Pat. No. 6,129,219; Kojima, et. al., Jan. 2, 2001; U.S. Pat. No. 5,157,158; Berna Tejero, et. al., Oct. 20, 1992; Waller, F. J., Catalysis With a Perfluorinated Ion-Exchange Polymer, ACS Symp. Ser. (1986), 308 (Polym. Reagents Catal.), 42-67; Haran, N. P., et. al., Catalysis by Ion Exchange Resins-Alkylation, 1978, Chem. Petro-Chem. J., v. 9, n. 7, p. 21-28; and Olah, G. A., et. al., Perflourinated Resinsulfonic Acid (Nafion®-H) Catalysts in Synthesis, 1986, Synthesis, v. 7, pp. 513-531 (all references listed in the application are incorporated herein in their entirety for all purposes.) The aromatic compound may be of the general formula

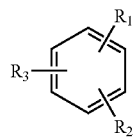

where naphthalene and any other polycyclic ring system may be substituted for benzene, and where $R_1$, $R_2$ and $R_3$ are independently selected from H, $C_1$-$C_6$ alkoxy, OH, $C_1$-$C_{36}$ alkyl, substituted $C_1$-$C_{36}$ alkyl and polyoxyalkylene ether. Branching of the alkyl group(s) may be in present in a variety of positions and as generally described in WO 00/43478; Scheibel, et. al.; pub. Jul. 27, 2000, which is incorporated herein by reference.

The term, "polycyclic ring systems," as used herein refers to aromatic hydrocarbons comprising 2, 3, 4, or 5 benzene rings that are optionally fused or attached via a single carbon-carbon bond. Examples include, but are not limited to biphenyl, 1-phenyl-naphthalene, naphthacene, 3H-benzo[de]anthracene, naphthalene, and anthracene. Polycyclic ring systems are optionally substituted with 1, 2, 3, or 4 groups that are independently selected from H, $C_1$-$C_6$ alkoxy, OH, $C_1$-$C_{36}$ alkyl, substituted $C_1$-$C_{36}$ alkyl and polyoxyalkylene ether. All alkyl groups may be linear or branched. Branching of the alkyl group(s) may be in present in a variety of positions and as generally described in WO 00/43478; Scheibel, et. al.; pub. Jul. 27, 2000, incorporated herein by reference.

AOS Acids

As used herein the term "AOS acid" (or alpha olefin sulfonic acid) means an acid material which is the reaction product of sulfonating an olefin, typically an alpha olefin, and generally comprises an alkene sulfonic acid, a sultone or a mixture thereof (the formulas for such materials are as previously described). Alkene sulfonic acid (or AOS acid which contains an appreciable amount of alkene sulfonic acid) is the precursor to alpha-olefin sulfonate or AOS which is a widely used surfactant with many applications for foaming, cleaning, emulsifying, and wetting. AOS acid is typically produced through the reaction of $SO_3$ with monoolefinic hydrocarbon, as shown for example, in U.S. Pat. Nos. 2,061,617; 2,572,605; and 3,444,191, all incorporated in the entirety herein. A process for producing high yields of alkene sulfonic acids is found in Weil, et. al., Journal of American Oil Chemists' Society (JAOCS), Vol. 41, October 1965, pp 873-875. The ratio of alkene sulfonic acid to sultone is from 1:1 to about 1:4 depending on manufacturing temperature, pressure, flow rates and other parameters known to those skilled in the art. The position of the double bond of the alkene sulfonic acid and the number of carbons in the sultone ring can also vary depending on these same parameters.

As an alternative embodiment, sultone based AOS acid, i.e., sultone which contains no alkene sulfonic acid or only trace amounts (less than 2 weight percent) of alkene sulfonic acid can be utilized in the alkylation methods described herein.

The processes of the invention generally do not require an AOS acid conversion step. As used herein, conversion is defined as the addition and removal of water in a cyclic fashion, with the application of heat (i.e. the crude acid is heated to just below its decomposition temperature), to and from the crude AOS acid to convert the sultone present in the crude acid mixture to alkene sulfonic acid prior to alkylation. Although less preferred and not required, the methods described can optionally further comprise digesting the AOS acid, optionally in the presence of water, and optionally in the presence of the aromatic compound, and removing said water prior to alkylation, such that the alkylation is conducted under substantially anhydrous conditions. As used herein, digestion is defined a thermal heating of alkene sulfonic acid (or sultone relative to the alkene sulfonic acid), for a limited period of time (i.e., about 1-120 minutes) at a temperature less than the decomposition temperature of the acid (i.e. 40-200° C.). However, digestion is distinct from conversion. In practicing digestion, water is not added and removed in a cyclic manner, as is the case with conversion. As a further distinction, digestion does not necessarily convert sultones to alkenes as is achieved with conversion; generally in the absence of water, thermal digestion actually may convert alkene sulfonic acids to sultones, an opposite effect of conversion.

As is well known to those of skill in the art, olefin starting materials, superacid catalysts and crude alkene sulfonic acids may be somewhat hygroscopic and inherently contain trace amounts of water.

Accordingly, the term "substantially anhydrous" as used herein for describing alkylation conditions denotes reaction mixtures which are basically free of added water, excepting trace amounts which are typically associated with the process reactants. Quantitatively, the term "substantially anhydrous" generally denotes a material which contains less than about 1% by weight of water, based on the weight of the crude AOS acid utilized.

Superacid Catalysts

In addition to those previous identified, the superacid catalysts useful herein are generally any superacid catalyst which is capable of catalyzing alkylation an aromatic compound with an AOS acid at a temperature sufficient to produce an arylalkylsulfonic acid, wherein the alkylation is conducted under substantially anhydrous conditions. Generally and in addition to those previously discussed, the superacid catalyst can be any one of those identified in U.S. Pat. No. 5,146,026; Berna Tejero, et. al., Sep. 8, 1992; U.S. Pat. No. 6,129,219; Kojima, et. al., Jan. 2, 2001; U.S. Pat. No. 5,157,158; Berna Tejero, et. al., Oct. 20, 1992; Waller, F. J., Catalysis With a Perfluorinated Ion-Exchange Polymer, ACS Symp. Ser. (1986), 308 (Polym. Reagents Catal.), 42-67; Haran, N. P., et. al., Catalysis by Ion Exchange Resins-Alkylation, 1978, Chem. Petro-Chem. J., v. 9, n. 7, p. 21-28; and Olah, G. A., et. al., Perflourinated Resinsulfonic Acid (Nafion®-H) Catalysts in Synthesis, 1986, Synthesis, v. 7, pp. 513-531. Further superacid catalysts are those identified in U.S. Pat. No. 5,304,688 ("the '688 patent) and U.S. Pat. No. 5,708,563; the definition of "superacid" as used herein is provided in the '688 patent, along with methods of measuring superacidity and various classes of suitable superacid catalysts.

Generally, the amount of super acid catalyst used is at least about 25% by weight, based on the amount of AOS acid. Ideally, the superacid catalyst is present in an amount of at least 100% by weight, based on the amount of AOS acid.

Alternative Catalyst Embodiments

The catalyst(s) used herein may be homogeneous or heterogeneous, with the later being particularly preferred, based upon ease of separation from the product and recycleability. Mixtures of superacids and an alkylation promoter may be utilized. Very strong anhydrous acids may be utilized alone or in combination with the superacids and/or alkylation promoter previously identified, provided that such use or combination is capable of catalyzing the alkylation of an aromatic compound with an AOS acid at a temperature sufficient to produce a predominantly monoalkylated arylalkylsulfonic acid, wherein the alkylation is conducted under substantially anhydrous conditions, without the need for conversion of the starting AOS acid. Very strong anhydrous acid catalysts are weaker in strength than traditional superacid catalysts. Examples of suitable optional very strong acid catalysts include any sulfonic acid type ion-exchange catalysts and catalyst resin systems which are capable of effectuation of the alkylation detailed herein, such as for example, Amberlyst-15, acidic zeolites, acidic clays or a mixture thereof. Other effective very strong acid catalysts include marcroreticular sulfonic acid polymers such as sulfonated poly(styrene-divinylbenezene) ion exchange resins.

The arylalkylsulfonic acids produced in accordance with the invention may be used "as is" or neutralized with a variety of bases such as NaOH, KOH, Ca(OH)$_2$, MgO$_2$, Ba(OH)$_2$, NH$_3$, monoethanol amine (MEA), diethanol amine (DEA), triethanol amine (TEA), isopropanol amine, and other amines, or mixtures of such bases, to form the corresponding sulfonates.

The arylalkylsulfonates are excellent surfactants, i.e., they are effective as surface and interfacial tension reducers, wetting agents, foaming agents and grease-cutting agents. The sulfonates can be used in cleaning and emulsion formulations, including hard surface cleaners, shampoos, body washes, liquid and powdered laundry detergent formulations, personal care cleansing formulations, water-in-oil emulsions, oil-in-water emulsions, and the like.

Within the scope of the present invention is included the combination of arylalkylsulfonic acids (AASA) and/or arylalkylsulfonates in compositions with formulating components that may be utilized to obtain formulations intended for fabric, hard surface and personal cleaning and/or care, and personal care applications, including anionic surfactants, non-ionic surfactants, amphoteric surfactants, hydrotropes, solvents, pine oils and other cleaning oils, antiredeposition agents, optical brighteners, enzymes, buffers, thickeners, builders, salts, chelating, agents, emollients, fragrances, dyes, cationic surfactants, biocidal agents, preservatives, emulsifiers, wetting agents, dispersing agents, pigments, and corrosion inhibitors.

The arylalkylsulfonates and AASAs can be further (or alternatively) blended with other traditional surfactants, such as nonionic that may include polyoxyalkylene ethers, amides, sacharrides, polysacharrides, oxides, and esters; cationics which may include quaternized nitrogen groups, anionics which may contain the functional groups of sulfate, sulfonate, phosphate, phosphonate, carboxylate, and acetate, and amphoteric/zwitterionic surfactants. The arylalkylsulfonates, AASAs or blends thereof may be formulated with traditional surfactants into a variety of end use products such as personal care compositions (shampoos, body washes, soap bars, etc.), hard surface cleaners, fabric cleaning and/or care compositions (liquids, heavy duty liquids, and powders), dish cleaning compositions (light duty liquids), oil-in-water emulsions, water-in-oil emulsions, and the like. These end use products may also contain various ingredients typically associated with them. The traditional surfactants, along with other application specific optional ingredients, which may be blended with the arylalkylsulfonates disclosed herein are those detailed in U.S. Pat. Nos. 6,218,346; 6,254,859; 6,172,026; 5,945,394; 5,746,945; 5,705,147; 5,637,758; and 5,616,781 all to Stepan Company, incorporated herein by the entirety.

Arylalkylsulfonates and/or AASA (can be used in emulsion polymerization, as agricultural surfactants, as emulsifiers, as oil field surfactants, as lubrication additives, as additives for metal working fluids, as additives for floatation applications, and as additives for drilling fluids.

The arylalkylsulfonic acid compositions comprise a compound of the formula I:

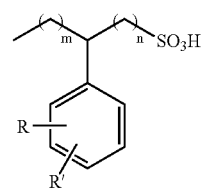

wherein m and n are independently integers 0 to 34, provided that m+n is at least 2 and wherein m+n is equal to or less than 34; wherein R and R' are independently selected from H, C$_1$-C$_6$ alkoxy, OH, C$_1$-C$_{36}$ alkyl, substituted C$_1$-C$_{36}$ alkyl and polyoxyalkylene ether.

The arylalkylsulfonic acid may further comprise a compound of the formula II:

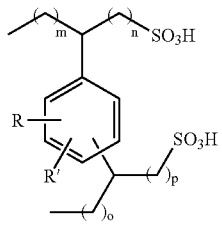

wherein m and n are independently 0-34, provided that m+n is at least 2 and wherein m+n is equal to or less than 34; wherein o and p are independently 0-34, provided that o+p is at least 2 and wherein o+p is equal to or less than 34; wherein R and R' are independently selected from H, $C_1$-$C_6$ alkoxy, OH, $C_1$-$C_{36}$ alkyl, substituted $C_1$-$C_{36}$ alkyl and polyoxyalkylene ether.

The arylalkylsulfonic acid may further comprise an AOS acid dimer compound of the formula III:

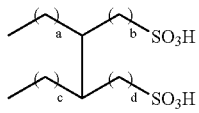

wherein a and b are independently 0-34, provided that a+b is at least 2 and wherein a+b is equal to or less than 34; wherein c and d are independently 0-34, provided that c+d is at least 2 and wherein c+d is equal to or less than 34. Although the above structure indicates a dimer acid connected by one carbon-carbon bond, two acid molecules may be connected together by two carbon-carbon bonds, thereby producing a cyclic type dimer acid (oligomeric acids are also contemplated).

The cleaning and/or care compositions may contain arylalkylsulfonates and/or AASAs. The cleaning and/or care composition may contain compounds of formulas I, II, and III, but compositions of formulas I and II, I and III, and II and III are also contemplated and within the scope of the invention.

The amount of active ingredient (arylalkylsulfonate and/or AASA) in the composition can range from about 0.1% by weight to about 90% by weight. More preferably the range is about 1% to about 60% by weight. Even more preferably the range is about 1% to about 40% by weight. One of skill in the art will recognize that the exact and the effective amount of active ingredient needed in a cleaning and/or care composition will depend on the intended use of the composition.

All documents, e.g., patents, journal articles and test methods, cited above or below are hereby incorporated by reference in their entirety. In the following examples, all amounts are stated in percent by weight of active material unless indicated otherwise. One skilled in the art will recognize that modifications may be made in the present invention without deviating from the spirit or scope of the invention. The invention is illustrated further by the following examples which are not to be construed as limiting the invention or scope of the specific procedures or compositions described herein. All levels and ranges, temperatures, results etc., used herein are approximations unless otherwise specified.

The terms listed below and as used herein have the following meanings and/or are supplied by the companies indicated

| Term | Definition |
| --- | --- |
| Nafion ® NR50 | Perflourosulfonic acid resin catalyst; available from Aldrich Chemical Company, Milwaukee, WI, and a registered trademark of E. I. duPont de Nemours & Co., Inc. |
| Nafion ® SAC-13 | 10-20 weight percent of Nafion Acidic polymer on a high surface area amorphous silica support; available from Aldrich Chemical Company, Milwaukee, WI, and a registered trademark of E. I. duPont de Nemours & Co., Inc. |
| Amberlyst ® 15 | Strongly acidic, macroreticular, sulfonated styrene-divinylbenzene copolymer ion-exchange resin; available from and a registered trademark of Rohm and Haas Co. |
| Zirconium Tungstate | ⅛" cylinders of $ZrO_2$ doped with 13% $WO_3$; Engelhard Corporation, Beachwood, OH |

EXAMPLE 1

This example demonstrates the utility of Nafion® NR50 perfluorosulfonic acid resin as a catalyst for the substantially anhydrous, high-yield preparation of $C_{12}$ benzene alkylsulfonic acid from AOS acid. To a 300 mL glass-lined autoclave were added 20.0 g (0.0805 moles) of crude $C_{12}$ alkene sulfonic acid (AOS Acid, EW=248.4), prepared via falling film reaction of 1-dodecene with $SO_3$, 112 mL of benzene, and 20 g of Nafion® NR50 perfluorosulfonic acid resin catalyst that had been previously dried under $N_2$ at 150° C. for 2 hours. As characterized by acid content and $^1H$ NMR analysis, the starting crude AOS acid was a mixture of approximately 60% sultones and 40% alkene sulfonic acids. In order to remove incidental water taken up by the AOS acid during handling, the reactor was heated to 120° C. with a single valve of the autoclave open to atmosphere and 40 mL of benzene and benzene/water azeotrope were distilled off from the reaction mixture. At this point, the reaction mixture contained 10 molar equivalents of benzene relative to AOS acid. The open valve was then closed and the reaction mixture was heated with stirring at 130° C. (30-40 p.s.i.) for 15 hours. Upon cooling, the reaction mixture was removed from the autoclave, filtered, and concentrated by vacuum rotary evaporation to afford a viscous, brown oil. Titration of the product with 0.1 N cyclohexylamine in methanol indicated 2.905 meq acid/g product (94% of the theoretical value of 3.063 meq acid/g for 100% $C_{12}$ benzene arylalkylsulfonic acid). $^1H$ NMR spectroscopy (methanol d-4) indicated high conversion of AOS acid during the reaction, as judged by the absence of peaks corresponding to alkene sulfonic acids (vinylic protons, δ 6.0-5.0 ppm) and a very minimal peak at δ 4.6 ppm, corresponding to sultone. Based on relative proton integration, the sultone content was estimated at less than 0.2%. The proton spectrum contained all of the expected features for $C_{12}$ benzene alkylsulfonic acid: δ 7.4-6.7, multiplet, 5.0 H, aromatic protons; δ 3.0-2.2, several sets of multiplets, 1.0 H, RC$\underline{H}$(phenyl)R'; δ2.8, multiplet, 2.0 H, RC$\underline{H}_2$SO$_3$H; δ 2.0-0.8, overlapping multiplets and triplets, alkyl $CH_2$ and $CH_3$. The presence of several sets of $^1H$ NMR multiplets for backbone R C$\underline{H}$(phenyl)R' protons indicates that there are multiple positional isomers (positions of attachment of the aromatic ring along the alkylsulfonic acid chain). Percent incorporation of benzene into the product was found to be 100% versus theory based on the 5.0 integration value for aromatic protons. This result suggests that dialkylation (reaction of benzene alkylsulfonic acid with second mole of AOS acid) and AOS dimerization and/or oligomerization occurred to only minor or minimal extents.

The recovered Nafion® NR50 catalyst was used repeatedly in more than 10 reactions under conditions identical to those described above. The catalyst was found to retain full activity without change in reaction product characteristics upon recycling.

EXAMPLE 2

This example demonstrates the utility of a dispersion of Nafion® NR50 on silica (i.e., Nafion® SAC-13) as a catalyst for the high-yield preparation of $C_{14-16}$ toluene alkylsulfonic acid from AOS acid.

For this reaction, $C_{14-16}$ AOS acid (EW=286), prepared via falling film reaction of a 65:35 ratio of $C_{14}/C_{16}$ alpha-olefins with $SO_3$, was used. Acid titration and $^1H$ NMR analysis indicated that this crude AOS acid was a mixture of approximately 60% sultones and 40% alkene sulfonic acids. To a 100 mL round bottom flask was added 11.0 g (0.0385 mole) of $C_{14-16}$ AOS acid, 35.4 g (0.385 mole) of toluene, and several Teflon boiling chips. The flask was fitted with a short-path still and 20.5 mL (0.192 mole) of toluene and toluene/water azeotrope were distilled from the solution in order to remove trace amounts of water. The remaining solution consisted of a 1:5 molar ratio of AOS acid to toluene. Upon cooling, 26.1 g of the solution (10.0 g of AOS acid) was transferred to a 50 mL round bottom flask, equipped with reflux condenser and $N_2$ inlet, that contained 10.0 of Nafion® SAC-13 catalyst. The catalyst had been previously dried under $N_2$ at 150° C. for 3 hrs. The reaction flask was heated to a constant ~116° C. reflux for 8 h. Over the course of reaction, the mixture lightened in color from dark purple to moderate reddish-brown. During the reaction, 0.2-0.5 g aliquots of liquid were removed periodically for analysis by titration with 0.1 N cyclohexylamine in methanol. Because the conversion of sultone to product resulted in a net mole equivalent generation of sulfonic acid per mole of sultone, the % of sultone converted in the mixture was calculated by interpolation between starting and final acid levels. Acid content in the reaction mixture versus time was as follows.

TABLE 1

| Time/Hours | meq acid/g in Rxn Mixture | % Sultone Converted |
|---|---|---|
| 0 | 0.5612 | 0 |
| 2 | 1.0715 | 71.5 |
| 4 | 1.2306 | 93.8 |
| 6 | 1.2746 | >99[a] |

[a]<0.5% sultone by $^1H$ NMR spectroscopy

Upon cooling, the reaction mixture was filtered, washing the catalyst with several portions of fresh toluene. The combined filtrates were concentrated by vacuum rotary evaporation to afford a brown, viscous oil. Titration of the product with 0.1 N cyclohexylamine in methanol indicated 2.533 meq acid/gram of product (theory for 100% $C_{14-16}$ toluene alkylsulfonic acid=2.645). $^1H$ NMR spectroscopic analysis indicated full conversion of AOS acid and exhibited all of the spectral features expected for $C_{14-16}$ toluene alkylsulfonic acid: δ 7.2-6.8, multiplet, 4.1 H, aromatic protons; δ 3.0-2.2, several sets of multiplets, 1.0 H, R C̲H(tolyl)R'; δ 2.8, multiplet, 2.0 H, RC̲H$_2$SO$_3$H; δ2.3, singlet, 3.0 H, R—ArC̲H$_3$, δ 2.0-0.8, overlapping multiplets, 28.9 H, alkyl CH$_2$ and CH$_3$. The normalized proton content of 4.1 aromatic protons and 3.0 tolyl—CH$_3$ protons relative to RCH$_2$SO$_3$H compares favorably to the theoretical value of 4.0 H (aromatic) and 3.0 H (tolyl—CH$_3$) for 100% toluene alkylsulfonic acid.

COMPARATIVE EXAMPLES A, B, C, AND D

These examples demonstrate the slow reaction rate and diminished selectivity for alkylation versus AOS acid oligomerization in the reactions of AOS acid with toluene without added catalyst. Reactions between crude $C_{14-16}$ AOS Acid and toluene were carried out in round bottom flasks (A and B) or in an autoclave (C and D), depending on temperature of reaction. Kinetics of reaction were monitored in terms of conversion of sultone to sulfonic acid, either by titration of aliquots with 0.1 N cyclohexylamine in methanol or by $^1H$ NMR spectroscopy. The following results were obtained:

TABLE 2

| Example | Mole Equivalents Toluene | Temp. (° C.) | Time (hours) | % Sultone Conversion[a] |
|---|---|---|---|---|
| A | 2 | 130 | 4 | -9.3 |
|   |   |   | 11 | 7.2 |
|   |   |   | 16 | 34.5 |
|   |   |   | 20 | 85.3 |
|   |   |   | 27 | ~99 |
| B | 13.4 | 110 | 4 | -1.3 |
|   |   |   | 9 | -8.5 |
|   |   |   | 13 | -15.6 |
| C | 5 | 150 | 4 | -22.3 |
|   |   |   | 20 | >99 |
| D | 2 | 150 | 4 | 13.2 |
|   |   |   | 20 | >99 |

[a]Negative value indicates net generation of sultone from alkene sulfonic acids.

The negative sultone conversions values indicate that there were net increases in total sultone in the reaction mixtures in the course of these reactions. These increases were due to the conversion of alkene sulfonic acids to sultones. As compared to the conversion versus time data provided in Example 2, where 93.8% conversion of sultone was achieved after 4 hours of reaction, the rater of sultone conversion for the uncatalyzed reactions were very slow, even at 150° C. Comparison of the 4 hour data points for comparative Examples C and D indicates that a major effect of increasing toluene molar equivalents relative to AOS acid was to decrease rate of sultone conversion to product.

For Examples A, C, and D, products were isolated by vacuum rotary evaporation. For these samples, $^1$HNMR spectroscopy indicated the absence of alkene sulfonic acids and only trace amounts of sultones. The sum of the integration values for the RCH$_2$SO$_3$H and RR'R"CH peaks (δ 3.2-2.1 H, minus integration due to ArCH$_3$) was set to 3.0 H. The normalized spectral data indicated that only 77-84% of the theoretical amount of toluene was incorporated into the products, which is substantially lower than the incorporation achieved in the superacid-catalyzed reaction described in Example 2. Information about the product compositions was obtained based on the assumption that possible side products include AOS dimer acids, resulting from the oligomerization of AOS acid, and toluene dialkylsulfonic acids, resulting from the dialkylation of toluene with 2 equivalents of AOS acid. The fraction of toluene dialkylsulfonic acid (dialkylate) in the aromatic-containing portion of the product was estimated crudely from the ratio of aromatic protons to tolyl—$CH_3$ protons. For 100% monoalkylate, this ratio has a theoretical value of 1.333 (4 protons/3 protons). For 100% dialkylate, the ratio has a theoretical value of 1.000 (3 protons/3 protons). The fraction of dialkylate in the aromatic-containing portion of the product was calculated as follows:

Fraction $ArCH_3$ as dialkylate=[1.333−(Ar$\underline{H}$ integration/Ar$\underline{CH}_3$ integration)]/0.333

Assigning $RCH_2SO_3H$ groups as a reference of 1 molar unit, molar quantities were calculated, recognizing that dialkylates and AOS acid dimers each contain 2 mole equivalents of sulfonic acid. These quantities were calculated as follows:

Mole $RSO_3H$=1.0

Mole $ArCH_3$=Ar$\underline{CH}_3$ integration/3

Mole dialkylate=Fraction $ArCH_3$ as dialkylate*Mole $ArCH_3$

Mole toluene alkylsulfonic acid=Mole $ArCH_3$−Mole dialkylate

Mole AOS dimer acid=[1.0−Mole toluene alkylsulfonic acid−(Mole dialkylate*2)]/2

By summing the molar quantities of toluene alkylsulfonic acid, dialkylate, and AOS dimer acid to give a total molar quantity, it was trivial to calculate mole fractions for each component. By far, the largest error in this analysis was the estimation of (Fraction $ArCH_3$ as dialkylate). Small errors in integration values could lead to large error in this estimation. Therefore, the composition of product in terms of dialkylate versus AOS must be viewed as qualitative. The results of the NMR analyses were as follows:

TABLE 3

| Example: | A | C | D |
|---|---|---|---|
| Integration: R$\underline{CH}_2SO_3H$ + RR'R"$\underline{CH}$ | 3.0 | 3.0 | 3.0 |
| Integration: Ar$\underline{CH}_3$ | 2.49 | 2.53 | 2.32 |
| Integration: Ar$\underline{H}$ | 3.27 | 3.33 | 3.06 |
| % Toluene Incorporation vs. Theory | 83 | 84 | 77 |
| Fraction of $ArCH_3$ as dialkylate | 0.0616 | 0.0578 | 0.0430 |
| Mole fraction toleuene alkylsulfonic acid | 0.875 | 0.886 | 0.851 |
| Mole fraction dialkylate | 0.057 | 0.054 | 0.038 |
| Mole fraction AOS dimer Acid | 0.067 | 0.059 | 0.111 |

COMPARATIVE EXAMPLE E

This example demonstrates the ineffectiveness of sulfuric acid as a catalyst for the reaction of $C_{14-16}$ AOS acid with toluene.

To a 250 mL round bottom flask equipped with magnetic stir bar and reflux condenser was added 10.0 g (0.035 mole) of crude $C_{14-16}$ AOS acid, 43.25 g (0.409 mole) of toluene, and 0.36 g (0.0035) of 95% sulfuric acid. The reaction mixture was refluxed (111° C.) and conversion was monitored in terms of acid content by titration of aliquots with 0.1 N cyclohexylamine in methanol. Results for this reaction and a control reaction without added sulfuric acid were as follows:

TABLE 4

| | meq acid/g | |
|---|---|---|
| Time/hours | $H_2SO_4$ Catalyst | No Catalyst |
| 0 | 0.3744 | 0.2613 |
| 2 | 0.2756 | 0.2811 |
| 6 | 0.2430 | 0.2381 |
| 10 | 0.2200 | 0.2210 |
| 13 | 0.2173 | 0.1998 |

Both the reaction with added $H_2SO_4$ and the control reaction exhibited substantial loss in acid content as a consequence of net generation of sultones from alkene sulfonic acids. These data clearly demonstrate that sulfuric acid was ineffective in promoting the conversion of sultones to arylalkylsulfonic acid.

EXAMPLES 3-6

These examples demonstrate the utility of superacidic materials as catalysts for the substantially anhydrous preparation of $C_{12}$ benzene alkylsulfonic acid from $C_{12}$ δ-sultone (1,4-sultone). Crude $C_{12}$ AOS acid was digested at 90° C. for 24 hours to convert all alkene sulfonic acid and gamma sultone (1,3-sultone) to delta sultone (1,4-sultone). The acid was then dissolved in a 50/50 mixture of ethanol and water and neutralized to pH>10 with sodium hydroxide. This solution was extracted with several portions of hexanes, and the combined extracts were dried over $MgSO_4$, filtered, and concentrated to a wax. The crude sultone was crystallized at −30° C. from hexanes (ca. 6:1 ratio hexanes to sultone), filtered while cold, and dried to afford high purity dodecene δ-sultone (dodecene-1,4-sultone) as a white, crystalline solid. The sultone contained less than 0.1% water, as determined by Karl Fischer titration.

For each reaction, 1 part dry catalyst, 1 part dodecene δ-sultone, and a specified amount of aromatic reagent (expressed in mol equivalents versus sultone), were reacted for a period of time sufficient to achieve >99% conversion of the sultone. After removal of the catalyst by filtration and concentration of the product by vacuum rotary evaporation, analysis of the product was conducted via $^1H$ NMR spectroscopy in methanol d-4. For all of these examples, the analyses indicated full conversion of sultone, no detectable amounts of alkene sulfonic acids, and structural features as expected for arylalkylsulfonic acids. Reaction conditions and results in terms of percent of theoretical aromatic incorporation into product were as follows:

TABLE 5

| Example | Catalyst | Equivalents of Aromatic (vs. Sultone) | Rxn Time (Hrs) | Rxn Temp. (° C.) | Aromatic Incorporation (% of theory) |
|---|---|---|---|---|---|
| 3 | Nafion ® NR50[a] | 10 eq. of benzene | 12 | 130 | 92% |
| 4 | Nafion ® NR50[a] | 13.4 eq. of toluene | 6 | 111 | 97% |
| 5 | Nafion ® NR50[a] | 10 eq. of phenol | 20 | 120 | 97% |
| 6 | Zirconium Tungstate[b] | 10 eq. of toluene | 11 | 111 | 95% |

[a]Dried for 2 hrs at 150° C.
[b]Engelhard Corporation, Beachwood, OH: ⅛" cylinders of $ZrO_2$ doped with 13% $WO_3$, calcined at 750-850° C. for 1 hr.

EXAMPLES 7-8

These examples demonstrate the negative effect of water on the kinetics of superacid catalyzed and uncatalyzed reactions of $C_{12}$ AOS acid with benzene. For each example, crude $C_{12}$ AOS acid, 1 mole equivalent of benzene, optional water, and optional catalyst were placed in a 23 mL poly-(tetrafluoroethylene)-lined acid digestion bomb (Parr Instrument. Company, Moline, Ill., part #4749). After sealing, the digestion bomb was placed in a 120° C. oven for 20 hours without stirring. Upon cooling, a small aliquot of the reaction mixture was concentrated under vacuum and the residue was analyzed by $^1H$ NMR spectroscopy in methanol d-4. Using the sultone ring proton at ~δ 4.6 ppm as an integration standard, estimates were made for the relative molar amounts of acid-equivalent units (sulfonic acid or anhydride) present in the reaction mixture as sultone (δ 4.6 ppm signal), alkene sulfonic acid (via vinylic protons), hydroxyalkane sulfonic acid (via δ 4.2 ppm signal), toluene alkylsulfonic acid (via aromatic proton signals), and the sum of dialkylates and AOS dimer acids (via accounting for the total alkyl chain proton integration after subtraction of the contributions of the other identified components). Reaction conditions and results in terms of percent conversion of AOS acid and selectivity for $C_{12}$ benzene alkylsulfonic acid were as follows:

TABLE 6

| Example | Catalyst | Wt % H$_2$O on AOS acid | % Conversion of AOS acid | % Selectivity for alkylsulfonic acid[a] |
|---|---|---|---|---|
| 7a | None | 0.063[b] | 67.4 | 14.6 |
| 7b | None | 0.5 | 64.5 | 13.4 |
| 7c | None | 2.0 | 39.2 | 12.9 |
| 8a | Nafion ® NR50[c] | 0.142[b] | 81.4 | 25.1 |
| 8b | Nafion ® NR50 | 0.5 | 78.4 | 18.8 |
| 8c | Nafion ® NR50 | 2.0 | 62.4 | 16.4 |

[a]Of the converted AOS acid, the percentage that was converted to benzene alkylsulfonic acid.
[b]Incidental water present in the AOS acid, as measured by Karl Fischer titration.
[c]Dried for 2 hrs at 150° C.

Comparison among the entries within Example 7 and within Example 8 indicates that increasing water content decreased both conversion of AOS acid and selectivity for benzene alkylsulfonic acid. These data exemplify the desirability of performing the reaction between AOS acid and an aromatic compound to afford arylalkylsulfonic acids under substantially anhydrous conditions. In addition, comparison of data between Examples 7 and 8 reveals that, even without any stirring, the presence of heterogeneous superacid catalyst improved both AOS acid conversion and selectivity for benzene alkylsulfonic acid.

EXAMPLE 9

This example demonstrates the utility of a strongly acidic ion-exchange resin as a catalyst for the high-yield preparation of $C_{12}$ toluene alkylsulfonic acid from AOS acid. To a 500 mL round bottom flask equipped with magnetic stir bar, toluene-pre-filled Dean-Stark trap, condenser, and $N_2$ inlet was added 95 g (0.382 mole) of crude $C_{12}$ alkene sulfonic (AOS) acid. In order to remove water adsorbed by the acid during storage and handling, the solution was heated to reflux for 30 minutes, collecting ~0.3 mL of water in the Dean-Stark trap. The trap was then replaced with a 23×2 cm column of dry molecular sieves and the solution was further refluxed until the condensation front reached the top of the column (approximately 15 minutes). Upon cooling, 40 mL (0.05 mole $C_{12}$ AOS acid and 0.25 mole toluene) of this dried solution was transferred under $N_2$ to a 250 mL 4-neck flask that was equipped with magnetic stir bar, thermocouple, condenser, $N_2$ inlet, and septum. To this flask was added 12.4 g of thoroughly washed and dried (115° C. under vacuum) Amberlyst® 15 catalyst. The mass ratio of AOS acid to catalyst was 1:1. The reaction mixture was then heated in a 130° C. oil bath for 6 h; the reflux temperature of the reaction mixture was 117-119°. Upon cooling, the reaction mixture was filtered, washing the catalyst with several portions of fresh toluene. The combined filtrates were concentrated by vacuum rotary evaporation (70° C., <250 mtorr) to afford a deep red, viscous oil. Titration of the product with 0.1 N cyclohexylamine in methanol indicated 2.736 milliequivalents of sulfonic acid per gram of product (theory for 100% $C_{12}$ toluene alkylsulfonic acid=2.937). $^1H$ NMR spectroscopy (methanol d-4) indicated complete conversion of AOS acid to the desired toluene alkylsulfonic acid, with aromatic incorporation corresponding to 102% of theory for monoalkylate product.

EXAMPLE 10

This example demonstrates the utility of linear alkylbenzenesulfonic acid as a catalyst for the reaction of AOS acid with an aromatic compound to afford a mixed sulfonic acid product. To a 500 mL round bottom flask equipped with magnetic stir bar, condenser, thermocouple, and $N_2$ inlet was added an azeotropically dried solution of 20.0 g (0.0805 mole) of $C_{12}$ AOS acid and 37.1 g (0.403 mole) of toluene. To this solution was added 54.5 g (0.171 mole) of linear alkylbenzenesulfonic acid (obtained by the falling-film sulfonation of linear alkylbenzene with $SO_3$; average chain length of $C_{11.4}$, MW=318.1) that had been dried by azeotropic distillation with toluene. The reaction mixture was then refluxed (129° C.) for 3 h. Periodic analysis of aliquots pulled from the reaction indicated that the acid content of the reaction mixture had leveled off after 2 h. Upon cooling, the product was isolated by vacuum rotary evaporation to afford a deep red, viscous oil. The acid content of the product was 2.995 milliequivalents acid/gram. $^1H$ NMR analysis indicated the expected product composition, with an approximately 2:1 ratio of linear alkylbenzenesulfonic acid to $C_{12}$ toluene alkylsulfonic acid.

EXAMPLE 11

This example demonstrates the utility of an AOS-acid digestion step prior to reaction with toluene as a means of improving the rate of reaction for the synthesis of arylalkysulfonic acid. To a 100 mL round bottom flask equipped with magnetic stir bar was added 15.0 g (0.0524 moles) of dry $C_{14-16}$ AOS acid. The flask was heated under $N_2$ at 150° C. for 1 hour. Upon cooling, 9.67 g (0.105 moles) of toluene was added, the flask was fitted with a reflux condenser and $N_2$ inlet, and the mixture was heated in a 130° C. oil bath until acid content had become constant. Sultone conversion for this reaction, together with a control reaction in which no digestion step had been used, was as follows:

TABLE 7

| Reaction Time | Approximate % Sultone Conversion | |
|---|---|---|
| (hours) | Example 15 | Control (no digestion) |
| 0 | 5 | 0 |
| 2 | 9 | −9 |
| 9 | 54 | −1 |
| 13 | 91 | |
| 14 | | 24 |
| 18 | 99 | 55 |
| 22 | | 99 |

EXAMPLES 12-15

These examples demonstrate the utility of using toluene alkysulfonic acid product from a previous reaction as a promoter for the reaction of AOS acid with toluene. For each example, $C_{14-16}$ toluene alkylsulfonic acid (low dialkylate and low AOS dimer acid content), prepared by Nafion® NR50-catalyzed reaction of AOS acid with toluene in a process comparable to those given in example 2, was used as a promoter in the reaction of $C_{14-16}$ AOS acid with toluene. Progress of reaction was monitored by cyclohexylamine titration of sulfonic acid that had been generated from the conversion of sultones in the AOS acid, taking into account the sulfonic acids already present in the reaction system from alkene sulfonic acid and the promoter acid. Reaction conditions and approximate sultone conversion were as follows:

TABLE 8

| | Example: | | | |
|---|---|---|---|---|
| | 12 | 13 | 14 | 15 |
| Reaction Temp. | 130 | 130 | 130 | 130 |
| Mole equivalents Toluene | 2 | 2 | 2 | 5 |
| Mole equivalents toluene alkylsulfonic acid as reaction promoter[a] | 0.25 | 1.0 | 2.0 | 2.0 |
| Reaction Time (hours): | Approx. % Sultone Conversion | Approx. % Sultone Conversion | Approx. % Sultone Conversion | Approx. % Sultone Conversion |
| 0.5 | 0 | <1 | 19 | 10 |
| 1 | −1 | 15 | 54 | 21 |
| 2 | −2 | 56 | 90 | 56 |
| 3 | −1 | 86 | >99 | 81 |
| 4 | 0 | 95 | | 91 |
| 5 | 2 | 98 | | >99 |
| 8 | | >99 | | |
| 10.5 | 24 | | | |
| 12 | 39 | | | |
| 15.5 | 82 | | | |
| 19 | 96 | | | |
| 23 | >99 | | | |

[a] One mole equivalent of toluene alkylsulfonic acid relative to AOS acid was equal to 1.32 mass equivalents.

It is apparent from the data that as the amount of toluene alkylsulfonic acid added to the reaction as a promoter was increased, the rate of sultone conversion increased dramatically. Comparative Example A provides data as a control reaction: relative to this control reaction, the presence of 0.25 mole equivalents of toluene alkylsulfonic acid (Example 12) afforded a noticeably improved rate of conversion. Comparison of data for Examples 14 and 15 indicate that an effect of increasing the equivalents of toluene used was to decrease the rate of sultone conversion.

The products of the reactions were isolated and analyzed by $^1$H NMR, utilizing the methods described in Comparatives examples A-D. The compositions identified were a reflection of the fate of both the AOS acid in the reaction and the toluene alkylsulfonic acid that was incorporated as a promoter. Negative mole fraction values for AOS dimer acids (which were evaluated based on subtraction of toluene alkylsulfonic acid and dialkylates from total acid) are a reflection of the errors associated with NMR integration and the computation methods used to calculate composition. The NMR analysis results were as follows:

TABLE 9

| | Example | | | |
|---|---|---|---|---|
| | 12 | 13 | 14 | 15 |
| Integration: RC$\underline{H}_2$SO$_3$H + RR'R"C$\underline{H}$ | 3.0 | 3.0 | 3.0 | 3.0 |
| Integration: ArC$\underline{H}_3$ | 2.60 | 2.68 | 2.64 | 2.92 |
| Integration: Ar$\underline{H}$ | 3.35 | 3.43 | 3.37 | 3.79 |
| % Toluene vs. theory for 100% toluene alkylsulfonic acid | 86 | 89 | 88 | 97 |
| Fraction of ArCH$_3$ as dialkylate | 0.137 | 0.155 | 0.167 | 0.113 |
| Mole fraction toluene alkylsulfonic acid | 0.856 | 0.860 | 0.846 | 0.927 |
| Mole fraction dialkylate | 0.136 | 0.158 | 0.170 | 0.118 |
| Mole fraction AOS dimer acid | 0.007 | −0.018 | −0.016 | −0.045 |

The above compositional analyses indicate that the method used in these examples was effective to providing mixtures of arylalkylsulfonic acids with minor, but significant, amounts of aryl dialkylsulfonic acids (dialkylates) and negligible amounts of AOS dimer acid. The presence of minor amounts of dialkylates was supported by the presence of small peaks in $^1$H NMR region of δ 6.9-6.65 ppm. These small peaks were minimal in products of very high toluene alkylsulfonic acid composition (for example, the product of Example 2).

EXAMPLE 16

This example demonstrates the utility of repeatedly using the products of previous syntheses of benzene alkylsulfonic acid to afford products that are substantially enriched in benzene dialkylsulfonic acids. To a 300 mL glass-lined autoclave was added 19.75 g (0.0795 mole) of crude $C_{12}$ AOS Acid, 74 g (0.947 mole) of benzene, and 51.89 g (0.159 mole) of $C_{12}$ benzene alkylsulfonic acid that had been previously prepared via the process described in Example 1. With a single valve of the autoclave open to atmosphere, the reactor was heated to 120° C. and 50 mL of benzene and benzene/water azeotrope were distilled off from the reaction mixture. At this point, the reaction mixture contained 5 molar equivalents of benzene relative to AOS acid. The reactor was cooled, an additional 50 mL of benzene was added, and the distillation of 50 mL of benzene and benzene/water azeotrope was repeated. The open valve was then closed and the reaction mixture was heated with stirring at 130° C. (30-40 p.s.i.) for 4 hours. Upon cooling, the product was isolated by vacuum rotary evaporation. The process was then repeated 3 times, each time using 51 grams of the product of the previous reaction to promote the reaction of 19.75 g of $C_{12}$ AOS acid with 5 mole equivalents of benzene.

The products from each cycle were characterized by $^1$H NMR in terms of mole fractions of $C_{12}$ benzene alkylsulfonic acid, benzene dialkylsulfonic acid (dialkylate), and AOS dimer acids. Unlike products derived from toluene, the aromatic signals for benzene alkylsulfonic acid (δ 7.34-7.09 ppm) and benzene dialkylsulfonic acid (δ 7.08-6.85 ppm) were resolved. Therefore, the relative amounts of mono- vs. dialkylate were readily calculated and were subject to less error than calculations for toluene-based products. To normalize integration values, δ 3.2-2.1 ppm ($RCH_2SO_3H$+ RR'R"CH) was set equal to 3.0 H. The molar equivalents of benzene alkylsulfonic acid, dialkylate, and AOS dimer acids were then calculated as follows:

Molar Equivalents:

Benzene alkylsulfonic acid=Integration ArH (δ 7.34-7.09ppm)/5.0

Dialkylate=Integration ArH (δ 7.08-6.85 ppm)/4.0

AOS dimer=[3.0−(benzene alkylsulfonic acid*3.0)−(dialkylate*6.0)]/6.0

By summing the molar equivalents, it was trivial to calculate mole fractions for each component. The results of NMR analyses were as follows:

TABLE 10

| | Reaction Cycle | | | |
|---|---|---|---|---|
| | 1 | 2 | 3 | 4 |
| Integration: $RCH_2SO_3H$ + RR'R"CH | 3.00 | 3.00 | 3.00 | 3.00 |
| Integration: ArH of Benzene Alkylsulfonic acid | 3.30 | 2.80 | 2.48 | 2.363 |
| Integration: ArH of dialkylate | 0.608 | 0.732 | 0.785 | 0.778 |
| Mole fraction benzene alkylsulfonic acid | 0.795 | 0.718 | 0.663 | 0.642 |
| Mole fraction dialkylate | 0.183 | 0.235 | 0.263 | 0.264 |
| Mole fraction AOS dimer acid | 0.022 | 0.048 | 0.074 | 0.094 |

The above compositional analyses indicate that the method used in these examples was effective to providing mixtures of arylalkylsulfonic acids with significant amounts of aryl dialkylsulfonic acids and lesser amount of AOS dimer acids. On a weight basis the product of cycle 4 contained 51% benzene alkylsulfonic acid, 37% benzene dialkylsulfonic acid, and 12% AOS dimer acid.

EXAMPLES 17-19

These examples demonstrate the utility of reacting AOS acid with arylalkylsulfonic acid in the absence of additional aromatic compounds to afford mixtures of arylalkylsulfonic acids, aryl dialkylsulfonic acids, and AOS dimer acids. For each reaction, arylalkylsulfonic acid that had been previously synthesized from $C_{12}$ AOS acid and an aromatic compound using Nafion® NR50 catalyst was used. Equimolar mixtures of these acids with $C_{12}$ AOS acid were reacted at elevated temperature until acid content became constant and were then analyzed by $^1$H NMR spectroscopy. Toluene-derived products were analyzed by the method described in Comparative Examples A-D, whereas benzene-derived products were analyzed by the method described in Example 16. The follow results were obtained:

TABLE 11

| | Example | | |
|---|---|---|---|
| | 17 | 18 | 19 |
| Aromatic | Toluene | Benzene | Benzene |
| Reaction Time (hours) | 2 | 20 | 1 |
| Reaction Temperature (° C.) | 130 | 100 | 150 |
| Mole Fraction Arylalkylsulfonic acid | 0.236 | 0.504 | 0.460 |
| Mole fraction dialkylate | 0.818 | 0.284 | 0.319 |
| Mole fraction AOS dimer acid | −0.055 | 0.212 | 0.222 |

As was discussed in Examples 12-15, a negative mole fraction value for AOS dimer acid (which was evaluated based on subtraction of toluene alkylsulfonic acid and dialkylates from total acid) is a reflection of the errors associated with NMR integration and the computation methods used to calculate composition for toluene-derived products. Even so, the spectroscopic data clearly supported a substantial conversion of starting material to dialkylate in the reaction of Example 17.

EXAMPLE 20

This example illustrates the useful surfactant properties of the sodium salts of arylalkylsulfonic acids prepared from the superacid catalyzed reaction of AOS acid with aromatic compounds.

Aqueous solutions of sodium salts of arylalkylsulfonic acids, synthesized via the reactions of AOS acids with aromatic compounds in methods comparable to those of Examples 1-2, were prepared by neutralization of the acids with sodium hydroxide in de-ionized (DI) water. Surface tensions of 0.1 wt % surfactant solutions in DI water were measured on an electrobalance tensiometer equipped with a platinum Wilhelmy plate after 2 h equilibration at 25° C. Foamability (initial foam height) and foam stability (foam height after 5 minutes) of 0.1 wt % surfactant solutions in DI water were determined at 25° C. utilizing the apparatus described in ASTM D 1173-53 "Standard Test Method for Foaming Properties of Surface-Active Agents." Wetting performance of 0.1 wt % surfactant solutions in DI water was evaluated at room temperature (22±3° C.) according to the method described in ASTM D 2281-68 "Standard Test Method for Evaluation of Wetting Agents by the Skein Test."

The following test results were obtained:

TABLE 12

| Sodium Salt | Surface Tension (dyne/cm) | Wetting Time (sec.) | Initial Foam Height (cm) | 5 min. Foam Height (cm) |
|---|---|---|---|---|
| $C_{12}$ Benzene Alkylsulfonic Acid | 40.2 | 25 | 16.5 | 16.5 |
| $C_{12}$ Toluene Alkylsulfonic Acid | 37.7 | 15 | 16.5 | 15.5 |
| $C_{12}$ Xylene Alkylsulfonic Acid | 35.9 | 20 | 17.0 | 16.5 |
| $C_{12}$ Cumene Alkylsulfonic Acid | 34.5 | 21 | 16.0 | 15.5 |
| $C_{14-16}$ Toluene Alkylsulfonic Acid | 36.5 | 41 | 15.5 | 15.5 |

The above data demonstrate that a variety of arylalkylsulfonic acid sodium salts exhibit good surface tension lowering properties, moderately good wetting performance, and very good foamability and foam stability properties.

EXAMPLE 21

This example demonstrates the useful detergent properties of the sodium salts of $C_{12}$ Benzene alkylsulfonic acids enriched in dialkylates and AOS dimer acids, as prepared by the method described in Example 16.

Aqueous solutions of sodium salts of sulfonic acids were prepared by neutralization of the acids with sodium hydroxide in de-ionized (DI) water. These surfactants were evaluated for their ability to clean artificially soiled fabrics by washing fabric swatches in 1 liter of 0.05 wt % solutions of the surfactants in 90 ppm 3:2 Ca/Mg hard water. A laboratory scale washing machine (Terg-o-tometer, United States Testing Co., 1415 Park Ave., Hoboken, N.J.) was utilized with the following test conditions: duplicate swatches of soiled fabrics, as specified in the table below, all swatch types combined in a single pot for a single surfactant; 100° F. wash water, ~80° F. rinse water; 100 RPM agitation; 10 minute wash, 5 minute rinse. Detergency was measured in terms of swatch color difference ($\Delta E$; larger values=greater detergency), which was calculated from photoelectric calorimeter data on swatches before and after washing as follows:

$$\Delta E = [(L_w - L_u)^2 + (a_w - a_u)^2 + (b_w - b_u)^2]^{1/2}$$

where:
L=reflectance
a=redness/greenness
b=yellowness/blueness
w=after washing
u=before washing The following detergency results were obtained:

TABLE 13

| | Detergency ($\Delta E$) | | | | |
|---|---|---|---|---|---|
| Sodium Salt | DS Cot[a] | DS PC[b] | DS Poly[c] | WFK Cot[d] | EMPA-101[e] |
| $C_{11.4}$ Linear Alkylbenzenesulfonic Acid | 4.83 | 3.31 | 3.56 | 2.34 | 7.63 |
| $C_{12}$ Benzene Alkylsulfonic Acid[g] | 4.43 | 3.87 | 4.48 | 2.34 | 6.63 |
| Example 16, Cycle #1 | 6.42 | 5.00 | 6.18 | 3.61 | 7.51 |
| Example 16, Cycle #2 | 6.04 | 4.84 | 5.87 | 3.42 | 7.11 |
| Example 16, Cycle #3 | 6.43 | 5.33 | 6.40 | 2.67 | 7.05 |
| Example 16, Cycle #4 | 6.56 | 5.44 | 7.26 | 2.83 | 7.67 |

[a]dust/sebum soil on cotton
[b]dust/sebum soil on polyester/cotton blend
[c]dust/sebum soil on polyester
[d]pigment (86% clay, 8% lampblack, 4% black iron oxide, 2% yellow iron oxide) and lanolin on cotton, Washerei Forschungs Institute of Krefeld, Germany
[e]carbon black and olive oil on cotton, Eldgenossiche Materials Prufungs Anstalt of St. Gall, Switzerland
[f]prepared via the method described in Example 1

The above data demonstrate that, relative to $C_{11.4}$ linear alkylbenzenesulfonic acid sodium salt (LAS), which is a widely utilized anionic surfactant for laundry and cleaning applications, $C_{12}$ benzene alkylsulfonic acid sodium salt displays comparable detergency performance in the unformulated single-surfactant tests. In addition, the above data illustrate the improved detergency of $C_{12}$ benzene alkylsulfonates that are enriched in dialkylates and AOS dimer acid salts, as produced by the method detailed in Example 16.

EXAMPLES 22-23 AND COMPARATIVE EXAMPLE F

These examples demonstrate the use of arylalkylsulfonic acids as surfactant ingredients in solvent-free all-purpose cleaner formulations.

Solvent-free all-purpose cleaner formulations were prepared using the ingredients listed in the table below:

TABLE 14

| Ingredient | Example 22 | Example 23 | Comparative Example F |
|---|---|---|---|
| Sodium Xylene Sulfonate (40% Active) | 1.38 g | 1.38 g | 1.39 g |
| Tetra-sodium EDTA[a] | 0.44 | 0.43 | 0.45 |
| Sodium metasilicate · $5H_2O$ | 0.22 | 0.21 | 0.21 |
| $C_{12}$ Benzene Alkylsulfonic acid | 0.88 | — | — |
| $C_{12}$ Toluene Alkylsulfonic acid | — | 0.88 | — |
| Ninol ® 11-CM[b] | — | — | 0.88 |
| Sodium Hydroxide (50% aqueous) | 0.11 | 0.13 | 0.11 |
| DI Water | 46.96 | 46.97 | 46.94 |
| Appearance | Clear Solution | Clear Solution | Clear Solution |
| pH | 10.49 | 11.37 | 11.97 |

[a]EDTA = ethylenediamine tetraacetic acid
[b]Ninol ® 11-CM is a detergent grade modified coco alkanolamide and is a registered trademark of the Stepan Company, Northfield, IL.

Examples 22 and 23 are comparable in composition to Comparative Example F, except that Ninol® 11-CM was replace with an equivalent amount of $C_{12}$ arylalkylsulfonic acid. In all three formulations, a clear solution was obtained, indicating good compatibility of the arylalkylsulfonic acids with the other formulating components.

EXAMPLES 24-25 AND COMPARATIVE EXAMPLE G

These examples demonstrate the use of arylalkylsulfonic acids as surfactant ingredients in all-purpose cleaner formulations.

Sovelnt-containing all-purpose cleaner formulations were prepared using the ingredients listed in the table below:

TABLE 15

| Ingredient | Example 24 | Example 25 | Comparative Example G |
|---|---|---|---|
| Propylene Glycol N-Butyl Ether | 0.69 g | 0.68 g | 0.69 g |
| Sodium Xylene Sulfonate (40% Active) | 0.88 | 0.89 | 0.88 |
| Tetra-sodium EDTA[a] | 0.46 | 0.46 | 0.46 |
| $C_{12}$ Benzene Alkylsulfonic acid | 0.67 | — | — |
| $C_{12}$ Toluene Alkylsulfonic acid | — | 0.69 | — |
| Ninol ® 11-CM[b] | — | — | 0.68 |
| Sodium Hydroxide (50% aqueous) | 0.15 | 0.15 | 0.10 |
| DI Water | 47.15 | 47.13 | 47.19 |
| Appearance | Clear Solution | Clear Solution | Clear Solution |
| pH | 11.36 | 11.25 | 12.28 |

[a]EDTA = ethylenediamine tetraacetic acid
[b]see Examples 22-23 for definition

Examples 24 and 25 are comparable in composition to Comparative Example G, except that Ninol® 11-CM was replace with an equivalent amount of $C_{12}$ arylalkylsulfonic acid. In all three formulations, a clear solution was obtained, indicating good compatibility of the arylalkylsulfonic acids with the other formulating components.

EXAMPLES 26-27 AND COMPARATIVE EXAMPLE H

These examples demonstrate the utility of arylalkylsulfonic acids as surfactant ingredients in pine oil cleaner concentrate formulations.

Pine oil cleaner concentrate formulations were prepared using the ingredients listed in the table below. Cleaning performance on vinyl tiles at room temperature was evaluated using ASTM D 4488-95, Annex A5, "Particulate and Oily Soil/Vinyl Tiles Test Method." This test used a modified Gardner Straight Line Washability Apparatus, as described in ASTM D 4488-95, Annex A4. The formulations were evaluated at 3.9 mL of concentrate diluted to 500 mL with DI water. Formulations and tests results were as follows:

TABLE 16

| Ingredient | Example 26 | Example 27 | Comparative Example H |
|---|---|---|---|
| Pine Oil | 10.03 g | 10.01 g | 10.01 g |
| Ninol® 11-CM[a] | 4.50 | 4.50 | 4.50 |
| Nonylphenol 12[b] | 2.50 | 2.50 | 2.50 |
| Lauramine Oxide (30% Active) | 0.25 | 0.25 | 0.25 |
| $C_{12}$ Benzene Alkylsulfonic acid | 1.00 | — | — |
| $C_{12}$ Toluene Alkylsulfonic acid | — | 1.00 | — |
| Dodecylbenzenesulfonic acid | — | — | 1.00 |
| Isopropanol | 5.00 | 5.00 | 5.00 |
| DI Water | 26.75 | 26.75 | 26.75 |
| Appearance | Clear Solution | Clear Solution | Clear Solution |
| pH | 8.95 | 9.05 | 8.95 |
| Gardner Straight Line Washability | | | |
| Average Percent Soil Removal | 72.9% | 81.7% | 73.7% |

[a]see Examples 22-23 for definition
[b]12 mole ethoxylate of nonylphenol

The above data demonstrate the utility of arylalkylsulfonic acids in Pine Oil cleaner concentrate formulations. Performance of the $C_{12}$ arylalkylsulfonic acid-containing formulations equaled or slightly surpassed the performance of the dodecylbenzenesulfonic acid (LAS) control formulation (Comparative Example H).

EXAMPLES 28-29 AND COMPARATIVE EXAMPLE I

These examples demonstrate the utility of arylalkylsulfonic acids as surfactant ingredients in economy light-duty liquid formulations for use as dish detergents.

Economy light-duty liquid formulations were prepared using the ingredients listed in the table below. Performance as dish-washing liquids was evaluated using the Mini-Plate Test, which is described in full in Example 1 of U.S. Pat. No. 5,637,758; to Sajic, et. al., Jun. 10, 1997. For each example, 6 g of a 10 wt % solution of formulation in DI water was diluted to 400 g with tap water. Formulations and tests results were as follows:

TABLE 17

| Ingredient | Example 28 | Example 29 | Comparative Example I |
|---|---|---|---|
| BIO-TERGE® AS-40[a] | 15.39 parts | 15.4 parts | 15.4 parts |
| STEOL® CS-460[b] | 9.0 | 9.0 | 9.0 |
| Cocamidopropyl Betaine (30% Active) | 4.0 | 4.0 | 4.0 |
| $C_{11.4}$ Linear Alkylbenzenesulfonic Acid | — | — | 1.0 |
| $C_{12}$ Benzene AASA | 1.02 | — | — |
| $C_{12}$ Toluene AASA | — | 1.0 | — |
| NaOH (50% aq.) | 0.406 | Q.S. | 0.294 |
| Sulfuric acid (10% aq.) | 0.02 | 0.02 | 0.06 |
| NaCl | 3.0 | 3.0 | 3.0 |
| DI Water | 70.6 | 70.6 | 70.6 |
| Total w/w | 100.0 | 100.0 | 100.0 |
| Appearance 25° C. | Clear liquid | Clear liquid | Clear liquid |
| pH (as is) 25° C. | 6.04 | 6.06 | 5.99 |
| Color Gardner | 2 | 1 | 1 |
| Viscosity (cps) 25° C. with 3% NaCl | 30 | 40 | 120 |
| Mini-Plate Test Performance | | | |
| Mini-plates washed | 15 | 15 | 18 |

[a]BIO-TERGE® AS-40 is a 40% active $C_{14-16}$ alpha olefin sulfonate and is a registered trademark of the Stepan Company, Northfield, IL
[b]STEOL® CS-460 is a 60% active sodium laureth sulfate with 3 moles of ethylene oxide and is a registered trademark of the Stepan Company, Northfield, IL The above data demonstrate the utility of arylalkylsulfonic acids in economy light-duty liquid formulations. Performance of the $C_{12}$ arylalkylsulfonic acid-containing formulations demonstrated minor difference in performance relative to the dodecylbenzenesulfonic acid (LAS) control formulation (Comparative Example I).

EXAMPLES 30-31 AND COMPARATIVE EXAMPLE J

These examples demonstrate the use of arylalkylsulfonic acids as surfactant ingredients in "Ultra" dish detergent formulations.

Light-duty liquid formulations, comparable to "Ultra" dish detergent formulations, were prepared using the ingredients listed in the table below:

TABLE 18

| Ingredient | Example 30 | Example 31 | Comparative Example J |
|---|---|---|---|
| $C_{11.4}$ Linear Alkylbenzenesulfonic Acid | — | — | 12.30 parts |
| $C_{12}$ Benzene AASA | 13.67 parts | — | — |
| $C_{12}$ Toluene AASA | — | 11.74 parts | — |
| Sodium Hydroxide (50% aq) | 3.03 | 2.4 | 3.03 |
| STEOL® CS-370[a] | 5.28 | 5.26 | 5.25 |
| ALPHA-STEP® MC-48[b] | 7.23 | 7.84 | 7.23 |
| Cocamidopropylamine oxide (33% Active) | 4.54 | 4.53 | 4.55 |
| Magnesium Sulfate, (27% aq) | 3.89 | 3.91 | 3.88 |
| Ethanol | 3.00 | 1.80 | 1.50 |
| Sodium Xylene Sulfonate (40% Active) | 3.03 | 3.00 | 3.00 |

TABLE 18-continued

| Ingredient | Example 30 | Example 31 | Comparative Example J |
|---|---|---|---|
| Propylene Glycol | 1.50 | 1.51 | 1.50 |
| Water | 24.69 | 16.77 | 8.69 |
| Citric Acid | 0.01 | — | — |
| Total w/w | 69.87 | 58.76 | 50.93 |
| Appearance 25° C. | Clear liquid | Clear liquid | Clear liquid |
| pH (as is) 25° C. | 6.98 | 7.00 | 6.93 |

[a]STEOL ® CS-370 is a 70% active sodium laureth sulfate with 3 moles of ethylene oxide and is a registered trademark of the Stepan Company, Northfield, IL
[b]ALPHA-STEP ® MC-48 is a 37% active mixture of sodium alpha-sulfo methyl $C_{12-18}$ Ester and sodium alpha-sulfo $C_{12-18}$ fatty acid salt, and is a registered trademark of the Stepan Company, Northfield, IL Examples 30 and 31 are comparable in composition to Comparative Example J, except that $C_{11.4}$ linear alkylbenzenesulfonic acid was replace with a similar amount of $C_{12}$ arylalkylsulfonic acid. In all three formulations, a clear solution was obtained, indicating good compatibility of the arylalkylsulfonic acids with the other formulating components.

EXAMPLES 32-33 AND COMPARATIVE EXAMPLE K

These examples demonstrate the use of arylalkylsulfonic acids as surfactant ingredients in "Premium Ultra" dish detergent formulations.

Light-duty liquid formulations, comparable to "Premium Ultra" dish detergent formulations, were prepared using the ingredients listed in the table below:

TABLE 19

| Ingredient | Example 32 | Example 33 | Comparative Example K |
|---|---|---|---|
| $C_{11.4}$ Linear Alkylbenzenesulfonic Acid | — | — | 12.13 parts |
| $C_{12}$ Benzene AASA | 13.57 parts | — | — |
| $C_{12}$ Toluene AASA | — | 15.61 parts | — |
| STEOL CS ® 460[a] | 9.01 | 9.00 | 9.00 |
| ALPHA-STEP ® MC-48[b] | 7.50 | 7.60 | 7.50 |
| NINOL ® 40-CO[c] | 2.25 | 2.25 | 2.25 |
| Sodium Hydroxide (50% aq.) | 3.11 | 3.20 | 3.115 |
| Ethanol | 1.0 | 1.00 | 1.00 |
| Citric Acid | 0.51 | 0.18 | 0.01 |
| DI Water | 15.39 | 29.49 | 15.385 |
| Total w/w | 52.34 | 68.33 | 50.39 |
| Appearance 25° C. | Clear liquid | Dark liquid | Clear liquid |
| pH (as is) 25° C. | 6.95 | 6.49 | 7.08 |
| Viscosity (cps) 25° C. | 850 | 1500 | 1100 |

[a]see Examples 28-29 for definition
[b]see Examples 30-31 for definition
[c]NINOL® 40-CO is a diethanolamine cocamide and is a registered trademark of the Stepan Company, Northfield, IL Examples 32 and 33 are comparable in composition to Comparative Example K, except that $C_{11.4}$ linear alkylbenzenesulfonic acid was replace with similar amounts of $C_{12}$ arylalkylsulfonic acid.

EXAMPLES 34-36

These examples demonstrate the use of arylalkylsulfonic acids as surfactant ingredients in heavy-duty laundry detergent powder formulations.

Powdered laundry detergent formulations were prepared in a laboratory blender using the ingredients listed in the table below. Detergent performance was evaluated using a method comparable to that described in Example 21. Test conditions were: 1.5 g of formulation in 1 L of 140-150 ppm hard water (2:1 Ca/Mg); duplicate swatches of soiled fabrics, as specified in the table below, all swatch types combined in a single pot for a single formulation; 100° F. wash water; 100 RPM agitation; 10 minute wash; hand rinse for 1 minute. Formulations and tests results were as follows:

TABLE 20

| Ingredient | Example 34 | Example 35 | Example 36 |
|---|---|---|---|
| Formulation Type | Premium | Economy | Economy |
| Soda Ash | 55.44 parts | 66.00 parts | 66.00 parts |
| Zeolite A[a] | 15.72 | 10.00 | 10.00 |
| Nonylphenol 10[b] | 2.10 | 2.00 | 2.00 |
| $C_{12}$ Toluene Alkylsulfonic acid | 14.40 | 12.00 | 0.00 |
| $C_{12}$ Benzene Alkylsulfonic acid | 0.00 | 0.00 | 12.00 |
| Sodium Metasilicate | 10.48 | 10.00 | 10.00 |
| SAVINASE ™ 16L type EX[c] | 0.62 | 0.00 | 0.00 |
| ALCO 3574[d] | 1.24 | 0.00 | 0.00 |
| Terg-O-Tometer Performance (Detergency (ΔE)) | | | |
| WFK/Cot[e] | 6.40 | 3.48 | 3.18 |
| WFK/PC[f] | 2.67 | 2.00 | 0.27 |
| DS/Cot[e] | 11.40 | 8.45 | 8.38 |
| DS/PC[e] | 21.02 | 20.39 | 17.14 |
| EMPA-116/Cot[g] | 35.12 | 20.14 | 18.97 |

[a]complex sodium aluminosilicate, "type A", 100% active powder
[b]10 mole ethoxylate of nonylphenol
[c]SAVINASE ™ 16L type EX is a protease enzyme with 16 KNPU/g activity and is a trademark of Novo Nordisk, Denmark
[d]anti-redeposition polymer, 40% active, Alco Chemical, a division of National Starch and Chemical Company, Chattanooga, TN
[e]see Example 21 for definition
[f]pigment (86% clay, 8% lampblack, 4% black iron oxide, 2% yellow iron oxide) and lanolin on polyester/cotton blend, Washerei Forschungs Institute of Krefeld, Germany
[g]blood, milk, and carbon black on cotton, Eldgenossiche Materials Prufungs Anstalt of St. Gall, Switzerland The above detergency results are indicative of good detergent performance and are comparable with the performance expected of respective linear alkylbenzenesulfonate-based premium and economy heavy-duty powder laundry detergent formulations.

EXAMPLES 37-40

These examples demonstrate the utility of arylalkylsulfonic acids as surfactant ingredients in unbuilt and built economy heavy-duty liquid laundry detergent formulations.

Liquid laundry detergent formulations were prepared using the ingredients listed in the table below. Detergent performance was evaluated using a method comparable to that described in Example 21. Test conditions were: 1.85 g of formulation in 1 L of 140-150 ppm hard water (2:1 Ca/Mg); duplicate swatches of soiled fabrics, as specified in the table below, all swatch types combined in a single pot for a single formulation; 100° F. wash water; 100 RPM agitation; 10 minute wash; hand rinse at 70° C.

TABLE 21

| Ingredient | Example 37 | Example 38 | Example 39 | Example 40 |
|---|---|---|---|---|
| Formulation Type | Unbuilt | Built | Unbuilt | Built |
| DI Water | 83.72 parts | 74.86 parts | 83.52 parts | 74.47 parts |
| Sodium Hydroxide (50% Aqueous) | 2.04 | 2.82 | 2.11 | 2.73 |
| $C_{12}$ Toluene Alkylsulfonic Acid | 9.27 | 11.98 | — | — |
| $C_{12}$ Benzene Alkylsulfonic Acid | — | — | 9.36 | 12.14 |
| Nonylphenol 9[a] | 4.97 | 6.39 | 5.00 | 6.50 |
| Soda Ash | — | 1.97 | — | 2.00 |
| Sodium Xylene Sulfonate (40%) | — | 1.98 | — | 2.16 |
| Total | 100 | 100 | 100 | 100 |
| Total Actives | 15 | 20 | 15 | 20 |
| pH (as-is) | 6.5 | 11.77 | 6.05 | 11.78 |
| Appearance | Clear, low-viscosity | Clear, viscous | Clear, low-viscosity | Clear, viscous |
| pH (in Terg-O-Tometer pot) | 7.61 | 8.87 | 7.64 | 8.86 |
| Terg-O-Tometer Performance (Detergency (□E)) | | | | |
| DS/Cot[b] | 6.07 | 7.88 | 6.91 | 6.88 |
| DS/Poly[b] | 4.05 | 7.17 | 4.21 | 4.17 |
| DS/PC[b] | 5.48 | 8.77 | 7.44 | 6.22 |
| WFK/Cot[b] | 4.12 | 4.70 | 4.66 | 3.45 |
| WFK/PC[c] | 2.89 | 5.25 | 4.20 | 4.14 |
| DMO/Cot[d] | 10.13 | 9.57 | 10.82 | 7.78 |

[a]9 mole ethoxylate of nonylphenol
[b]see Example 21 for definition
[c]see Examples 34-36 for definition
[d]dirty motor oil on cotton The above detergency results are indicative of good detergent performance and are comparable with the performance expected of respective linear alkylbenzenesulfonate-based economy heavy-duty liquid detergent formulations.

EXAMPLES 41-42

These examples demonstrate the utility of arylalkylsulfonic acids as surfactant ingredients in premium heavy-duty liquid laundry detergent formulations.

Liquid laundry detergent formulations were prepared using the ingredients listed in the table below. Detergent performance was evaluated using a method comparable to that described in Example 21. Test conditions were: 1.68 g of formulation in 1 L of 140-150 ppm hard water (2:1 Ca/Mg); duplicate swatches of soiled fabrics, as specified in the table below, all swatch types combined in a single pot for a single formulation; 100° F. wash water; 100 RPM agitation; 10 minute wash; hand rinse at 70° C. Formulations and tests results were as follows:

TABLE 22

| Ingredient | Example 41 | Example 42 |
|---|---|---|
| DI $H_2O$ | 50.42 parts | 49.61 parts |
| Sodium Hydroxide (50% aqueous) | 1.95 | 2.11 |
| Optical Brightener | 0.10 | 0.10 |
| Calcium Chloride | 0.05 | 0.06 |
| $C_{12}$ Toluene Alkylsulfonic Acid | 8.86 | — |
| $C_{12}$ Benzene Alkylsulfonic Acid | — | 8.86 |
| Propylene Glycol | 4.73 | 4.76 |

TABLE 22-continued

| Ingredient | Example 41 | Example 42 |
|---|---|---|
| Boric Acid | 0.95 | 0.95 |
| Sodium Laureth Sulfate (60% Active) | 18.55 | 18.60 |
| Nonylphenol 9[a] | 10.66 | 10.70 |
| Fragrance | 0.11 | 0.11 |
| Dye (1% Solution) | 0.01 | 0.01 |
| SAVINASE ™ 16L type Ex[b] | 0.057 | 0.58 |
| TERMAMYL ® 300L type DX[c] | 0.29 | 0.29 |
| ISP PVP K30[d] | 0.95 | 0.96 |
| ALCO 3564[e] | 0.47 | 0.47 |
| Sodium Xylene Sulfonate (40% Active) | 1.86 | 1.86 |
| Total | 100 | 100 |
| Total Actives | 31 | 31 |
| pH (as-is) | 8.87 | 8.70 |
| Appearance | Hazy, viscous | Hazy, viscous |
| pH (in Terg-o-tometer pot) | 7.94 | 7.93 |
| Terg-O-Tometer Performance (Detergency ΔE)) | | |
| DS/Cot[f] | 10.62 | 10.62 |
| DS/PC[f] | 9.93 | 10.08 |
| WFK/Cot[f] | 4.90 | 4.40 |
| WFK/PC[b] | 3.98 | 3.55 |
| Grass/Cot[g] | 8.64 | 9.09 |
| EMPA 111[h] | 15.95 | 15.12 |

[a]9 mole ethoxylate of nonylphenol
[b]see Examples 34-36 for definition
[c]TERMAMYL ® 300L type DX is an alpha-amylase enzyme with 300 KNU/g activity and is a registered trademark of Novo Nordisk, Denmark
[d]Polyvinylpyrrolidone, 66.8 × 10³ molecular weight, International Specialty Products, New Jersey
[e]anti-redeposition polymer, 40% active, Alco Chemical, a division of National Starch and Chemical Company, Chattanooga, TN
[f]see Example 21 for definition
[g]grass soil on cotton
[h]blood on cotton, Eldgenossiche Materials Prufungs Anstalt of St. Gall, Switzerland The above detergency results are indicative of good detergent performance and are comparable with the performance expected of linear alkylbenzenesulfonate-based premium heavy-duty liquid detergent formulations.

Arylalkylsulfonic acids may be used as surfactant ingredients in hand soap formulations. Representative hand soap formulations, as described in table 23, were prepared using the ingredients listed in the table below.

TABLE 23

| | Hand soap formulations | |
|---|---|---|
| Component | A | B |
| $C_{12}$ Toluene | 20.6 | — |
| $C_{14-16}$ Toluene | — | 16.97 |
| STEOL ® CS-460 | 9.0 | 9.0 |
| AMPHOSOL ® CA | 4.0 | 4.0 |
| NINOL ® 40-CO | 1.0 | 1.0 |
| D.I. Water | 65.4 | 69.03 |
| Total: | 100.0 | 100.0 |
| PH adjusted 5.5-6.5 | 6.20 | 6.20 |
| Appearance* after pH adjusted | Clear yellow | Clear yellow |

Arylalkylsulfonic acids may be used as surfactant ingredients in gel shampoo formulations. Representative gel shampoo formulations, as described in table 24, were prepared using the ingredients listed in the table below.

TABLE 24

Low pH Gel Shampoo formulations

| Component | A | B | C | D |
|---|---|---|---|---|
| C$_{14-16}$ Benzene (17.2%) | 51.16 | — | — | — |
| C$_{12}$ Benzene (23.8%) | — | 36.97 | — | — |
| C$_{12}$ Toluene (29.9%) | — | — | 29.43 | — |
| C$_{14-16}$ Toluene (36.3%) | — | — | — | 24.24 |
| AMPHOSOL ® CA | 14.0 | 14.0 | 14.0 | 14.0 |
| AMMONYX ® CDO SPECIAL | 5.0 | 5.0 | 5.0 | 5.0 |
| Citric Acid (pH 4-5) | q.s | q.s | q.s | q.s |
| D.I. Water | 29.84 | 44.03 | 51.57 | 56.76 |
| Total: | 100.0 | 100.0 | 100.0 | 100.0 |
| pH adjusted (4-5) | 4.96 | 4.95 | 4.97 | 4.25 |
| Appearance* after pH adjusted | Opaque light yellow | Opaque amber | Opaque light yellow | Opaque off white |

*All were clear at higher pH.

Arylalkylsulfonic acids may be used as surfactant ingredients in body wash formulations. Representative body wash formulations, as described in table 25, were prepared using the ingredients listed in the table below.

TABLE 25

Body Wash formulations

| Component | A | B |
|---|---|---|
| D.I. Water | 17.33 | 26.18 |
| C12 Toluene | 50.17 | — |
| C14-16 Toluene | — | 41.32 |
| NINOL ® 55-LL | 4.0 | 4.0 |
| STEOL ® CS-330 | 28.5 | 28.5 |
| Total: | 100.0 | 100.0 |
| PH adjusted 6-6.5 | 6.22 | 6.15 |
| Appearance* after pH adjusted | Clear gold liquid | Gel |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for preparing arylalkylsulfonic acid of the formula

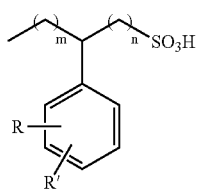

wherein m and n are independently integers 0 to 34, provided that m+n is at least 2 and wherein m+n is equal to or less than 34; wherein R and R' are independently selected from H, $C_1$-$C_6$ alkoxy, OH, $C_1$-$C_{36}$ alkyl, substituted $C_1$-$C_{36}$ alkyl and polyoxyalkylene ether, providing a reaction mixture comprising one or more aromatic compounds, one or more alpha olefin sulfonic (AOS) acids and one or more alkylation promoters and alkylating said one or more aromatic compounds with said one or more alpha olefin sulfonic acids in the presence of said one or more alkylation promoters, wherein the one or more aromatic compound is selected from the group consisting of benzene, toluene, xylene, cumene, phenol, alkylphenol alkylated on one or more carbons, alkoxylated phenol, benzene wherein the benzene is optionally substituted with 1, 2, or 3 groups that are independently selected from H, $C_1$-$C_6$ alkoxy, OH, $C_1$-$C_{36}$ alkyl, substituted $C_1$-$C_{36}$ alkyl and polyoxyalkylene ether, and mixtures thereof:

wherein the one or more alpha olefin sulfonic (AOS) acids are acid materials which are the reaction product of sulfonating an olefin; and wherein the one or more alkylation promoters comprises a compound of the formula:

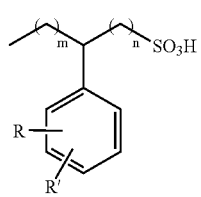

wherein m and n are independently integers 0 to 34, provided that m+n is at least 2 and wherein m+n is equal to or less than 34; wherein R and R' are independently selected from H, $C_1$-$C_6$ alkoxy, OH, $C_1$-$C_{36}$ alkyl, substituted $C_1$-$C_{36}$ alkyl and polyoxyalkylene ether;

wherein the alkylation is conducted at a temperature sufficient to produce an arylalkylsulfonic acid; under substantially anhydrous conditions; and the alkylation promoter is initially present in at least 25% by weight, based on the weight of the alpha olefin sulfonic (AOS) acid that is present.

2. A method for preparing an arylalkylsulfonic acid to claim 1, further comprises a compound of the formula

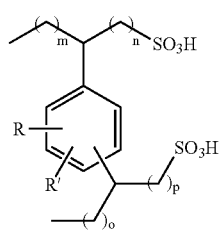

wherein m and n are independently 0-34, provided that m+n is at least 2 and wherein m+n is equal to or less than 34; wherein o and p are independently 0-34, provided that o+p is at least 2 and wherein o+p is equal to or less than 34; and wherein R and R' are independently selected from H, $C_1$-$C_6$ alkoxy, OH, $C_1$-$C_{36}$ alkyl, substituted $C_1$-$C_{36}$ alkyl and polyoxyalkylene ether.

3. A method for preparing an arylalkylsulfonic acid according to claim 2, further comprising an alkylation promoter of the formula:

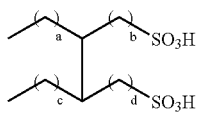

wherein a and b are independently 0-34, provided that a+b is at least 2 and wherein a+b is equal to or less than 34; wherein c and d are independently 0-34, provided that c+d is at least 2 and wherein c+d is equal to or less than 34.

4. A method according to claim 1, wherein the aromatic compound is selected from the group consisting of benzene wherein the benzene is optionally substituted with 1, 2, or 3 groups that are independently selected from H, $C_1$-$C_6$ alkoxy, OH, $C_1$-$C_{36}$ alkyl, substituted $C_1$-$C_{36}$ alkyl and polyoxyalkylene ether.

5. A method according to claim 4, wherein the aromatic compound is selected from the group consisting of phenol, alkylphenol alkylated on one or more carbons, and alkoxylated phenol.

6. A method according to claim 4, wherein the aromatic compound is selected form the group consisting of benzene, toluene, xylene, cumene, ethylbenzene, propylbenzene, and mixtures thereof.

7. A method according to claim 4, wherein the aromatic compound is selected from the group consisting of benzene, toluene, or xylene.

8. A method according to claim 1, wherein the alpha olefin sulfonic (AOS) acid comprises an alkene sulfonic acid, a sultone or a mixture thereof.

9. A method according to claim 8, wherein the sultone is of the formula:

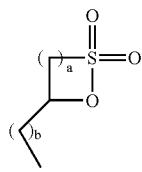

and wherein the alkene sulfonic acid is of the formula:

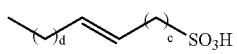

wherein a is 1, 2 or 3 and b is an integer of from 1 to 31; and wherein c and d are independently 0 or an integer from 1 to 33, where c+d=1 to 33.

10. A method according to claim 8, wherein the alpha olefin sulfonic (AOS) acid comprises the alkene sulfonic acid and the sultone in a molar ratio of alkene sulfonic acid to sultone of from about 1:1 to about 1:4.

11. A method according to claim 1, wherein the molar ratio of aromatic compound to alpha olefin sulfonic (AOS) acid is from about 0.5:1 to about 30:1.

12. A method according to claim 11, wherein the molar ratio of aromatic compound to alpha olefin sulfonic (AOS) acid is from about 2:1 to about 10:1.

13. A method according to claim 1, wherein the arylalkylsulfonic acid of the formula:

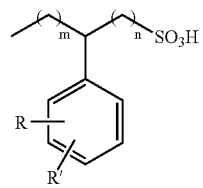

wherein
m and n are independently 0 or integers from 1 to 34, provided that m+n is at least 2 and less than or equal to 34; wherein R and R' are independently selected from H, $C_1$-$C_6$ alkoxy, OH, $C_1$-$C_{36}$ alkyl, substituted $C_1$-$C_{36}$ alkyl and polyoxyalkylene ether.

14. A method according to claim 13, wherein the arylalkylsulfonic acid further comprises a compound of the formula:

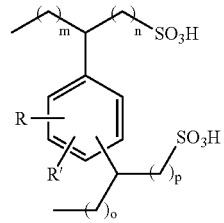

wherein m and n are independently 0-34, provided that m+n is at least 2 and equal to or less than 34; wherein o and p are independently 0-34, provided that o+p is at least 2 and equal to or less than 34; and wherein R and R' are independently selected from H, $C_1$-$C_6$ alkoxy, OH, $C_1$-$C_{36}$ alkyl, substituted $C_1$-$C_{36}$ alkyl and polyoxyalkylene ether.

15. A method according to claim 14, wherein the arylalkylsulfonic acid further comprises adding an alpha olefin sulfonic (AOS) acid dimer compound of the formula:

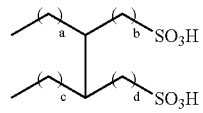

wherein a and b are independently 0-34, provided that a+b is at least 2 and equal to or less than 34; wherein c and d are independently 0-34, provided that c+d is at least 2 and equal to or less than 34.

16. A method according to claim 1, wherein the alkylation is conducted at a temperature from about 80° C. to about 200° C.

17. A method according to claim 16, wherein the alkylation is conducted at a temperature from about 100° C. to about 150° C.

18. A method according to claim 1, wherein the alkylation promoter is present initially in at least 75% by weight, based on the weight of the alpha olefin sulfonic (AOS) acid that is present.

19. A method according to claim 1, wherein the alkylation promoter is present initially in at least 100% by weight, based on the weight of the alpha olefin sulfonic (AOS) acid that is present.

* * * * *